United States Patent
Song et al.

(10) Patent No.: US 10,299,763 B2
(45) Date of Patent: May 28, 2019

(54) ULTRASOUND IMAGING APPARATUS AND METHOD OF CONTROLLING THE SAME

(71) Applicant: SAMSUNG MEDISON CO., LTD., Gangwon-do (KR)

(72) Inventors: Min Jung Song, Daejeon (KR); Jae Moon Jo, Seongnam-si (KR); Chul An Kim, Yongin-si (KR); Min Ju Lee, Seoul (KR); Gil-Ju Jin, Seoul (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 0 days.

(21) Appl. No.: 15/093,463

(22) Filed: Apr. 7, 2016

(65) Prior Publication Data

US 2017/0112472 A1   Apr. 27, 2017

(30) Foreign Application Priority Data

Oct. 26, 2015   (KR) ........................ 10-2015-0148494

(51) Int. Cl.
*A61B 8/08*   (2006.01)
*A61B 8/00*   (2006.01)
(Continued)

(52) U.S. Cl.
CPC ............ *A61B 8/5215* (2013.01); *A61B 8/085* (2013.01); *A61B 8/0833* (2013.01);
(Continued)

(58) Field of Classification Search
CPC ..... A61B 8/0875; A61B 8/0891; A61B 8/467; A61B 8/5207; A61B 5/0422;
(Continued)

(56) References Cited

U.S. PATENT DOCUMENTS 6,285,898 B1 *   9/2001   Ben-Haim ........... A61B 5/0215
128/899
6,685,644 B2 *   2/2004   Seo ..................... A61B 8/0833
128/916

(Continued)

FOREIGN PATENT DOCUMENTS

EP   2922025 A1   9/2015

OTHER PUBLICATIONS

Extended European Search Report dated Mar. 1, 2017 issued in European Patent Application No. 16158996.5.

*Primary Examiner* — Jingge Wu

(74) *Attorney, Agent, or Firm* — Morgan Lewis & Bockius LLP

(57) ABSTRACT

Disclosed herein is an ultrasound imaging apparatus for dividing obtained ultrasound image information into pieces of image information in units of regions of a human body, mapping a body marker to the pieces of image information corresponding to the body marker, and outputting a result of mapping the body marker to the pieces of image information; and a method of controlling the same. The ultrasound imaging apparatus includes an image processor configured to obtain image information from an object, a controller configured to divide the obtained image information into pieces of image information in units of regions of a human body and map a body marker to the pieces of image information corresponding to the body marker, and a user interface unit configured to output a result of mapping the body marker to the pieces of image information.

12 Claims, 16 Drawing Sheets

(51) Int. Cl.
*G06F 3/041* (2006.01)
*G06T 7/00* (2017.01)
*G06T 7/11* (2017.01)

(52) U.S. Cl.
CPC .......... *A61B 8/0875* (2013.01); *A61B 8/0891* (2013.01); *A61B 8/463* (2013.01); *A61B 8/467* (2013.01); *A61B 8/483* (2013.01); *A61B 8/5207* (2013.01); *A61B 8/54* (2013.01); *G06F 3/041* (2013.01); *G06T 7/0012* (2013.01); *G06T 7/11* (2017.01); *A61B 8/0858* (2013.01); *A61B 8/4405* (2013.01); *A61B 8/468* (2013.01); *A61B 8/5223* (2013.01); *G06T 2207/10132* (2013.01); *G06T 2207/30204* (2013.01)

(58) Field of Classification Search
CPC ....... A61B 5/0215; A61B 90/39; A61B 8/463; A61B 2090/3966; A61B 2090/3995; A61B 5/066; A61B 8/465; A61B 8/483; A61B 8/5215; A61B 8/00; A61B 8/085; A61B 8/468; A61B 8/5261; G06T 2207/10132; G06T 2207/30204; G06T 7/0012; G06T 7/11; G06T 7/73
See application file for complete search history.

(56) References Cited

U.S. PATENT DOCUMENTS

| | | | |
|---|---|---|---|
| 7,806,824 B2* | 10/2010 | Ohtake | A61B 8/00 600/407 |
| 8,837,792 B2 | 9/2014 | Gleichman et al. | |
| 2009/0124906 A1* | 5/2009 | Caluser | A61B 5/06 600/443 |
| 2010/0191114 A1* | 7/2010 | Hyun | A61B 8/00 600/443 |
| 2012/0157842 A1 | 6/2012 | Davis et al. | |
| 2012/0165671 A1* | 6/2012 | Hill | A61B 8/0883 600/443 |
| 2013/0172746 A1* | 7/2013 | Lee | A61B 8/4263 600/443 |
| 2013/0322719 A1* | 12/2013 | Dekel | A61B 6/12 382/131 |
| 2014/0181716 A1* | 6/2014 | Merritt | A61B 5/0066 715/771 |
| 2014/0276045 A1 | 9/2014 | Lee et al. | |
| 2015/0245882 A1* | 9/2015 | Venkatraghavan | A61B 6/503 600/424 |
| 2015/0278993 A1 | 10/2015 | Yamazaki et al. | |
| 2016/0174944 A1* | 6/2016 | Song | A61B 8/5215 600/453 |

* cited by examiner

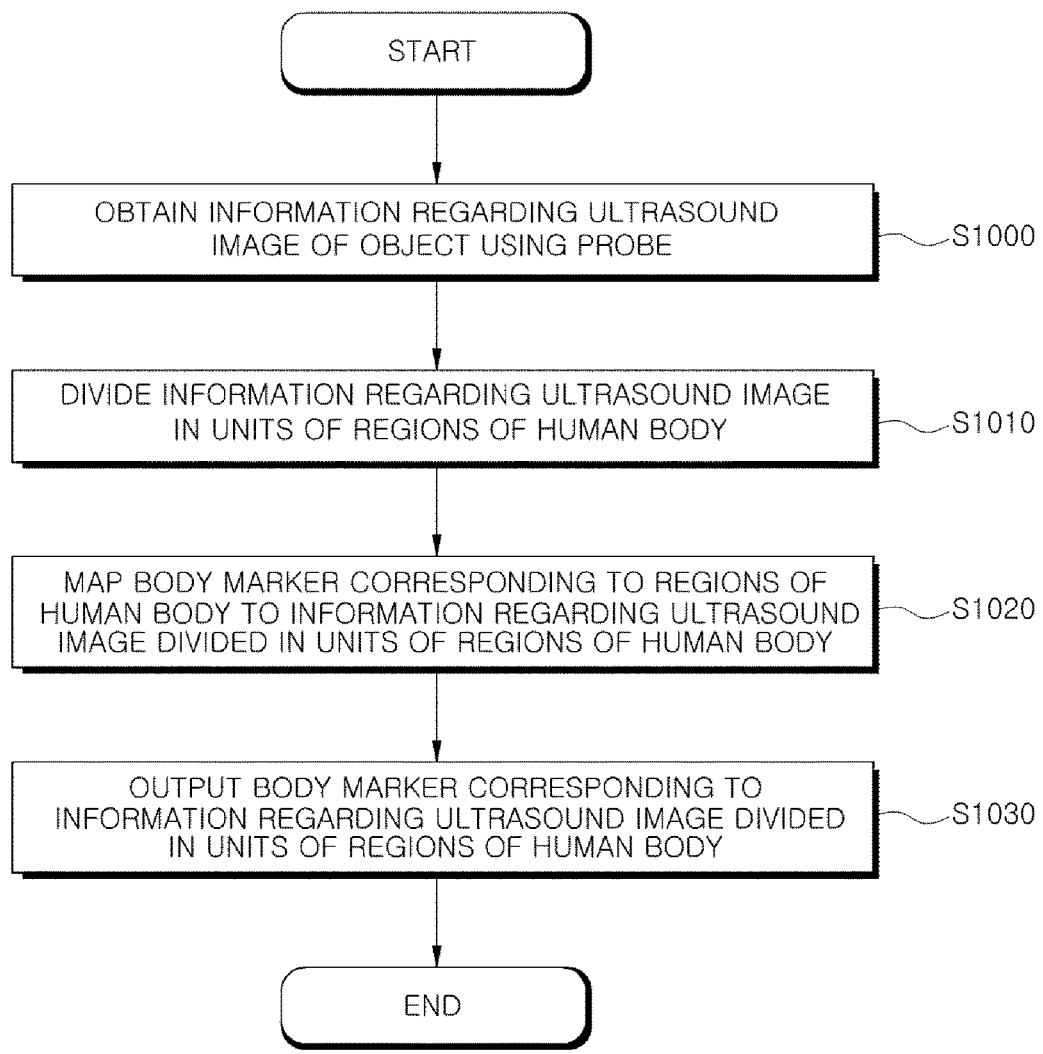

ULTRASOUND IMAGING APPARATUS AND METHOD OF CONTROLLING THE SAME

CROSS-REFERENCE TO RELATED APPLICATION

This application claims the benefit of Korean Patent Application No. 10-2015-0148494, filed on Oct. 26, 2015 in the Korean Intellectual Property Office, the disclosure of which is incorporated herein by reference.

BACKGROUND

1. Field

Embodiments of the present invention relate to an ultrasound imaging apparatus and a method of controlling the same.

2. Description of the Related Art

An ultrasound imaging apparatus is used for a medical purpose, e.g., to observe the inside of an object, detect a foreign substance, measure an injury, etc., by irradiating an ultrasound signal generated by a transducer of a probe from a skin of the object to a target region inside the body and receiving information of an ultrasound signal (an ultrasound echo signal) reflected from the target region to noninvasively obtain a tomographic image of a soft tissue of the target region or an image of a blood flow.

The ultrasound imaging apparatus has a small size, is cheap, is capable of displaying images in real time, and is free from radiation exposure and thus very safe compared to other image diagnosis apparatuses such as an X-ray diagnostic apparatus, an X-ray computerized tomography (CT) scanner, a magnetic resonance image (MRI) apparatus, a nuclear medicine diagnosis apparatus, etc. Thus, the ultrasound imaging apparatus has been widely used together with other image diagnostic apparatuses.

The ultrasound imaging apparatus provides not only an ultrasound image but also various diagnostic information using an image, a body marker, etc. However, the ultrasound imaging apparatus displays the shape of a complicated organ in the simplified form of a cross-sectional image. Thus when a diagnostician and an image interpreter are different, it is highly probable that an image will be erroneously interpreted, making detecting a region of a human body from an ultrasound image difficult.

SUMMARY

Therefore, it is an aspect of the present invention to provide an ultrasound imaging apparatus capable of providing a body marker containing diagnostic information, reference information, and reference annotation information rather than a body marker of a simple reference image, and matching the body marker with regions of a human body in an ultrasound image, thereby enabling a user to have an intuition regarding a direction and regions of a scan image. It is another aspect of the present invention to provide an ultrasound imaging apparatus capable of providing such information to increase user convenience, and a method of controlling the same.

Additional aspects of the invention will be set forth in part in the description which follows and, in part, will be obvious from the description, or may be learned by practice of the invention.

In accordance with one aspect of the present invention, an ultrasound imaging apparatus includes an image processor configured to obtain image information from an object; a controller configured to divide the obtained image information into pieces of image information in units of regions of a human body and map a body marker to the pieces of image information corresponding to the body marker; and a user interface unit configured to output a result of mapping the body maker to the pieces of image information.

The controller may divide the obtained image information in units of the regions of the human body using at least one among a line, a plane, and a color.

The controller may increase or decrease, according to a user input, sizes of portions of the pieces of image information of the image information divided in units of the regions of the human body.

The controller may divide the obtained image information into at least one among images of a bone, a blood vessel, a nerve, a muscle, and a ligament of the object.

The user interface unit may output the body marker, which is mapped to the pieces of image information of the image information divided in units of the regions of the human body, in the form of at least one among a cross-sectional image, a two-dimensional (2D) image, and a three-dimensional (3D) image.

The user interface unit may output the body marker in the form of a plurality of layers such that the plurality of layers of the body marker are mapped to the pieces of image information of the image information divided in units of the regions of the human body.

The ultrasound imaging apparatus may further include a user input unit configured to input information to the body marker output in the form of the plurality of layers.

The information input to the body marker including the plurality of layers may include at least one of diagnostic information, reference information, reference image information, and reference annotation information.

The controller may modify the information input to the body marker output in the form of the plurality of layers.

In accordance with another aspect of the present invention, a method of controlling an ultrasound imaging apparatus includes obtaining image information from an object; dividing the obtained image information into pieces of image information in units of regions of a human body; mapping a body marker to the pieces of image information corresponding to the body marker and outputting a result of mapping the body marker to the pieces of image information.

The dividing of the obtained image information into the pieces of image information in units of the regions of the human body may include dividing the obtained image information in units of the regions of the human body using at least one among a line, a plane, and a color.

The dividing of the obtained image information into the pieces of image information in units of the regions of the human body may include increasing or decreasing, according to a user input, sizes of portions of the pieces of image information of the obtained image information divided in units of the regions of the human body.

The dividing of the obtained image information into the pieces of image information in units of the regions of the human body may include dividing the obtained image information into at least one among images of a bone, a blood vessel, a nerve, a muscle, and a ligament of the object.

The outputting of the result of mapping the body marker to the pieces of image information may include outputting the body marker, which is mapped to the pieces of image information of the image information divided in units of the regions of the human body, in the form of at least one among a cross-sectional image, a two-dimensional (2D) image, and a three-dimensional (3D) image.

The outputting of the result of mapping the body marker to the pieces of image information may include outputting the body marker in the form of a plurality of layers such that the plurality of layers of the body marker are mapped to the pieces of image information of the image information divided in units of the regions of the human body.

The method may further include inputting information to the body marker output in the form of the plurality of layers.

The inputting of the information to the body marker output in the form of the plurality of layers may include inputting at least one among diagnostic information, reference information, reference image information, and reference annotation information.

The mapping of the body marker to the pieces of image information may include modifying the information input to the body marker output in the form of the plurality of layers.

BRIEF DESCRIPTION OF THE DRAWINGS

These and/or other aspects of the invention will become apparent and more readily appreciated from the following description of the embodiments, taken in conjunction with the accompanying drawings of which:

FIG. 3 is a flowchart of a process of outputting a body marker using an ultrasound imaging apparatus in accordance with one embodiment of the present invention;

DETAILED DESCRIPTION

Figure 1:
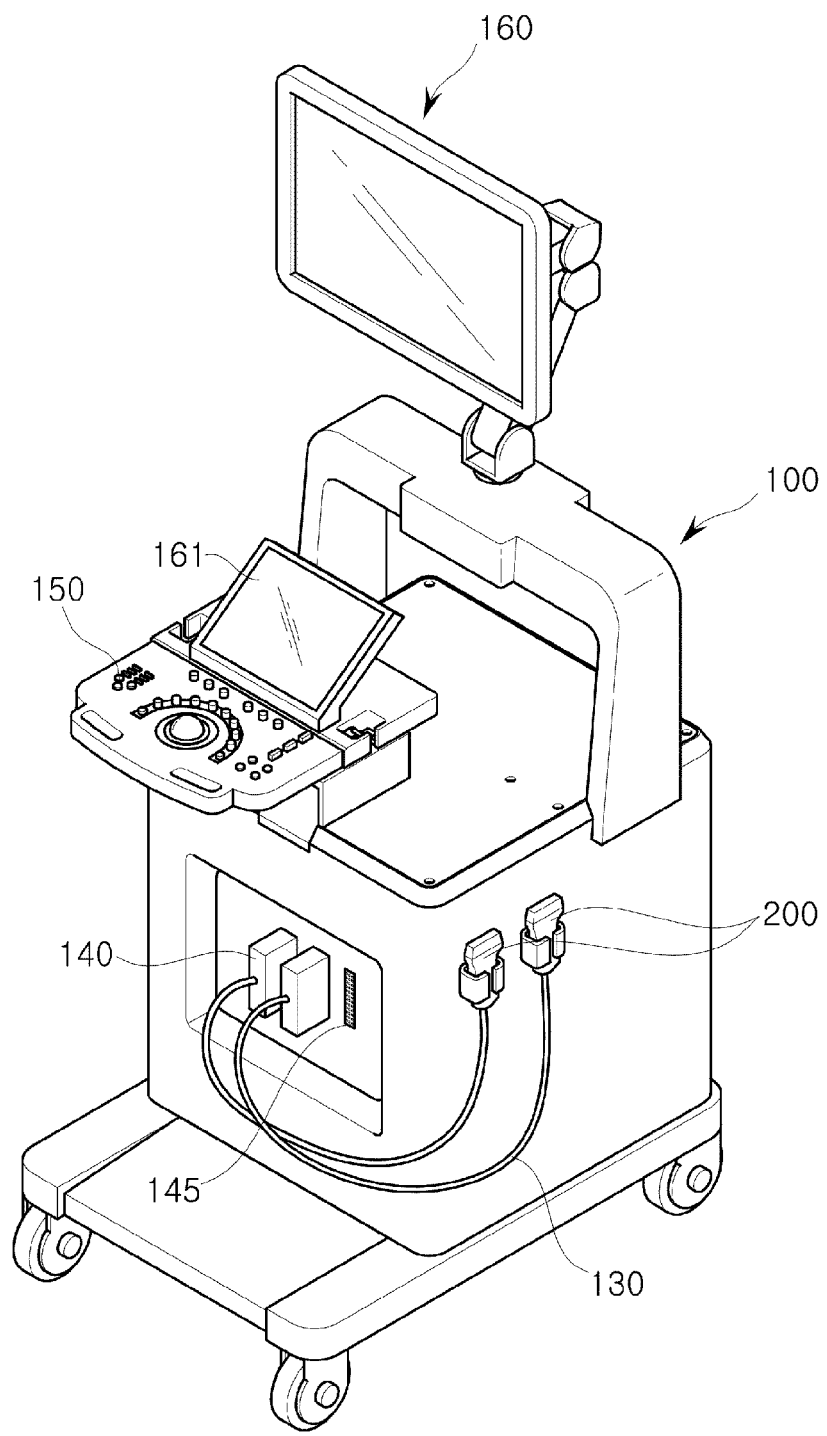
FIG. 1 is a perspective view of the exterior of an ultrasound imaging apparatus in accordance with one embodiment of the present invention.

The advantages and characteristics of the present invention and a method of achieving them will be apparent from exemplary embodiments set forth herein, taken in conjunction with the accompanying drawings.

The exemplary embodiments set forth in the present disclosure and the drawings are merely examples of the present invention. It should be understood that various modified examples that replace exemplary embodiments and drawings of the present invention would have been made at the filing date of the present application.

Hereinafter, an ultrasound imaging apparatus and a method of controlling method thereof in accordance with exemplary embodiments of the present invention will be described in detail. Like reference numerals denote like elements in the drawings and are thus not redundantly described here.

Throughout the present disclosure, the term 'object' should be understood to cover a human, an animal, or a part of a human or an animal. Examples of the object may include an organ such as a liver, a heart, a womb, a brain, a breast, an abdomen, etc. or a blood vessel. The term 'user' may be understood as a doctor, a nurse, a medical laboratory technician, a medical image specialist, a technician who repairs medical apparatuses, etc. but is not limited thereto.

Throughout the present disclosure, the term 'ultrasound image' means an image of an object obtained using ultrasonic waves but may be understood also as an image of an object obtained using an X-ray diagnostic apparatus, a computerized tomography (CT) scanner, a magnetic resonance image (MRI) apparatus, a nuclear medicine diagnosis apparatus, etc. A diagnostic apparatus in which an ultrasound imaging apparatus and a method of controlling the same in accordance with an embodiment may be applied or used may be an X-ray photographing apparatus, an X-ray fluoroscopy apparatus, a CT scanner, an MRI apparatus, a positron emission tomography apparatus, and an ultrasound imaging apparatus. Exemplary embodiments set forth herein will be described with respect to an ultrasound imaging apparatus but are not limited thereto.

The term 'body marker' means a model representing a location or an object on which ultrasonic waves are irradiated, etc. In general, examples of a body marker include a model of a liver which is an internal organ of a human body, a model of a bone, a muscle, or a ligament of an arm of the human body, etc.

Exemplary embodiments of the present invention will now be described in detail with reference to the accompanying drawings so that those of ordinary skill in the technical field to which the present invention pertains can easily accomplish them. However, the present invention may be embodied in many different forms and is not limited to the exemplary embodiments set forth herein. For clarity, elements that are not related to describing the exemplary embodiments are omitted in the drawings.

Hereinafter, exemplary embodiments of the present invention will be described in detail with reference to the accompanying drawings.

FIG. 1 is a perspective view of the exterior of an ultrasound imaging apparatus in accordance with one embodiment of the present invention.

As illustrated in FIG. 1, the ultrasound imaging apparatus includes a body 100, and a user input unit 150, a display unit 160, a sub-display panel 161, and an ultrasound probe 200 which are coupled to the body 100.

A plurality of casters (not shown) may be provided at a bottom of the body 100 of the ultrasound imaging apparatus to move the ultrasound imaging apparatus. The plurality of casters may be configured to fix the ultrasound imaging apparatus to a specific location or move the ultrasound imaging apparatus in a specific direction. The ultrasound imaging apparatus described above is referred to as a cart-type ultrasound imaging apparatus.

The ultrasound imaging apparatus may be a portable ultrasound imaging apparatus that can be carried by a user when the user moves to a distant location, unlike in FIG. 1. In this case, the plurality of casters may not be included in the portable ultrasound imaging apparatus. For example, the portable ultrasound imaging apparatus may be a fax viewer, a smart phone, a laptop computer, a personal digital assistant (PDA), a tablet personal computer (PC), etc. but is not limited thereto.

The ultrasound probe 200 is configured to be in contact with a skin of an object and may transmit ultrasonic waves to or receive ultrasonic waves from the object. In detail, the ultrasound probe 200 may generate ultrasonic waves according to an input pulse, transmit the ultrasonic waves into the object, and receive echo ultrasonic waves reflected from a specific location in the object.

The body 100 of the ultrasound imaging apparatus may transmit an ultrasound signal to the ultrasound probe 200, receive an echo ultrasound signal from the ultrasound probe 200, and generate an ultrasound image based on the echo ultrasound signal.

The generated ultrasound image may be provided to a user via the display unit 160. The user may diagnose the object, i.e., a patient, by viewing an ultrasound image of the inside of the object provided via the display unit 160.

The display unit 160 may display various user interfaces (UIs) related to controlling an ultrasound apparatus. A user may view a UI provided via the display unit 160, and input a control command for the ultrasound imaging apparatus or one element of the ultrasound imaging apparatus via the user input unit 150.

Also, the display unit 160 may display ultrasound images obtained during an ultrasound diagnosis process. The display unit 160 may be embodied as one of well-known embodiments thereof, e.g., a cathode ray tube (CRT), a liquid crystal display (LCD), etc., and may provide not only two-dimensional (2D) images but also three-dimensional (3D) images.

A user may touch the display unit 160 to input a control command for the ultrasound imaging apparatus and to input a touch command for setting a region of interest in an ultrasound image of an object, which the user wants to observe or diagnose. Also, the user may touch the display unit 160 displaying an ultrasound image of an object to set a region of interest in the ultrasound image.

Thus, the display unit 160 may include a touch panel configured to receive a touch input from a user. The touch panel may be embodied as an LCD panel, a light-emitting diode (LED) panel, an organic light-emitting diode (OLED) panel, or the like.

The sub-display unit 161 may display various UIs related to controlling the ultrasound imaging apparatus, similar to the display unit 160. A user may view a UI provided via the sub-display unit 161 and input a control command for the ultrasound imaging apparatus or one element of the ultrasound imaging apparatus via the user input unit 150 or a touch screen of the sub-display unit 161.

Also, the sub-display unit 161 may display ultrasound images obtained during an ultrasound diagnosis process. A user may touch the sub-display unit 161 to input a control command for the ultrasound imaging apparatus or a command to set a region of interest in an ultrasound image.

The user input unit 150 is a means configured to receive data from a user for controlling the ultrasound imaging apparatus. The user input unit 150 may include hardware elements such a keypad, a mouse, a touch panel, a touch screen, a trackball, a jog switch, etc. but is not limited thereto. The user input unit 150 may further include various means of input, such as an electrocardiogram measuring module, a respiration measuring module, a voice recognition sensor, a gesture recognition sensor, a fingerprint recognition sensor, an iris recognition sensor, a depth sensor, a distance sensor, etc.

Also, a user may input, via the user input unit 150, a command to start a diagnosis, a command to select a part to be diagnosed, a command to select a type of a diagnosis, a command to select a mode of an ultrasound image to be finally output, etc.

The ultrasound probe 200 may be connected to one end of a cable 130. Another end of the cable 130 may be connected to a male connector 140. The male connector 140 connected to the other end of the cable 130 may be physically coupled to a female connector 145 of the body 100.

One ultrasound probe 200 may be connected to one body 100 according to the above method. Similarly, a plurality of ultrasound probe 200 may be connected to one body 100. To this end, a plurality of female connectors may be installed on the body 100. FIG. 1 illustrates a case in which two ultrasound probes 200 are connected to one body 100.

Alternatively, the ultrasound probe 200 may be wirelessly connected to the body 100, unlike in FIG. 1. In this case, the ultrasound probe 200 wirelessly transmits an echo ultrasound signal corresponding to an echo ultrasonic wave received from an object to the body 100.

The ultrasound probe 200 may come in contact with a skin of an object to transmit an ultrasonic wave to or receive an ultrasonic wave from the object. In detail, the ultrasound probe 200 irradiates an ultrasonic wave into the object according to an ultrasound signal which is an electrical signal received from the body 100, collects an echo ultrasonic wave reflected from a specific location in the object, and transmits an echo ultrasound signal corresponding to the echo ultrasonic wave to the body 100.

To this end, the ultrasound probe 200 may include a transducer and a MUltipleXer (MUX) circuit. The transducer may include a plurality of elements that vibrate to convert an electrical signal into an ultrasonic wave or convert an ultrasonic wave to an electrical signal.

The plurality of elements may be arranged on one surface of a housing of the ultrasound probe 200. In detail, a plurality of transducers may be arranged in parallel to an aperture formed in one surface of the housing so that an ultrasonic wave may be transmitted or received via the aperture.

One embodiment of the present invention disclosed herein will be described in detail with reference to the accompanying drawings.

Figure 2:
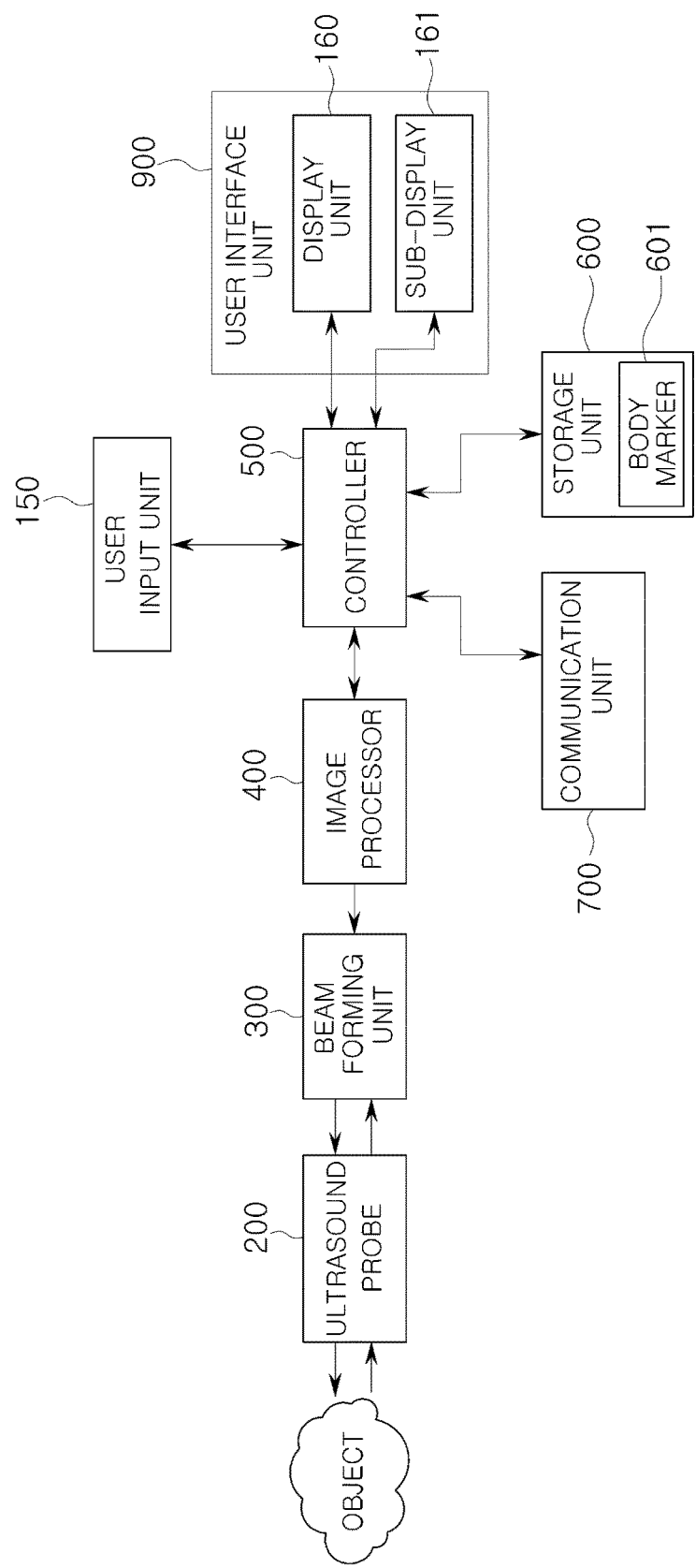
FIG. 2 is a block diagram of an ultrasound imaging apparatus in accordance with one embodiment of the present invention.

FIG. 2 is a block diagram of an ultrasound imaging apparatus in accordance with one embodiment of the present invention.

Referring to FIG. 2, the ultrasound imaging apparatus in accordance with an embodiment of the present invention may include a user input unit 150, an ultrasound probe 200, a beam forming unit 300, an image processor 400, a controller 500, a storage unit 600, a communication unit 700, and a user interface unit 900. However, not all of these elements are indispensable elements. The ultrasound imaging apparatus may further include other elements or may include only some of the elements illustrated in FIG. 2.

The user input unit 150 may input a control command for the ultrasound imaging apparatus or one element of the ultrasound imaging apparatus as described above with reference to FIG. 1. Via the user input unit 150, a user may select pieces of image information of an ultrasound image displayed on a display unit 160 or a sub-display unit 161 divided in units of regions of a human body, or a body marker corresponding to the pieces of image information. The body marker corresponding to the pieces of information may include a plurality of layers according to the pieces of image information divided in units of the regions of the human body.

Also, a user may input, via the user input unit 150, information regarding each of the regions of the human body into a body marker output in the form of a plurality of layers.

In this case, the information input to the body marker via the user input unit 150 including the plurality of layers may include at least one among diagnostic information (such as the name and symptoms of a disease, a method of curing the disease, etc.), other reference information, reference image information, and reference annotation information.

Also, a user may input a command to set a region of interest of an ultrasound image via the user input unit 150. Also, the user may input, via the user input unit 150, a control command to increase or decrease the size of the pieces of image information divided in units of the regions of the human body.

However, inputting a control command for the ultrasound imaging apparatus or one element of the ultrasound imaging apparatus by a user is not limited to using the user input unit 150 and may be performed by touching the user interface unit 900 as will be described below.

The ultrasound probe 200 may be variously embodied within a scope of a technique of obtaining volume data of an object. The ultrasound probe 200 is configured to be in contact with a skin of an object to transmit an ultrasonic wave to or receive an ultrasonic wave from the object.

In detail, the ultrasound probe 200 generates an ultrasonic wave according to an input pulse, transmits the ultrasonic wave into the object, and receives an echo ultrasonic wave reflected from a specific location in the object.

Thus, the ultrasound imaging apparatus may generate an ultrasound image of an object, based on an echo ultrasonic signal received from the object.

The beam forming unit 300 may perform beam forming to collimate an ultrasonic wave transmitted to or received from the ultrasound probe 200. The beam forming unit 300 may include a transmission beam former (not shown) and a reception beam former (not shown) to convert an analog signal into a digital signal or a digital signal into an analog signal and to control the time difference between ultrasonic waves transmitted or received from at least one transducer.

The beam forming unit 300 may be included in the ultrasound imaging apparatus body 100 as illustrated in FIG. 2 but may be included in the ultrasound probe 200 to perform a function thereof.

The beam forming unit 300 may employ one of well-know beam forming methods or may apply a combination of beam forming methods among the well-know beam forming methods or selectively apply the well-know beam forming methods.

The image processor 400 may receive beam-forming data from the beam forming unit 300, and transmit the data to the controller 500 to process an image. Also, the image processor 400 may obtain ultrasound image information from an object by processing a beam-formed echo ultrasound signal. Also, the image processor 400 may process an echo ultrasound signal according to one of well-known image processing methods.

For example, the image processor 400 may perform time-gain compensation (TGC) on a beam-formed echo ultrasound signal. Then, the image processor 400 may set a dynamic range (DR).

After setting the dynamic range, the image processor 400 may compress an echo ultrasound signal of the set dynamic range. Lastly, the image processor 400 may rectify the echo ultrasound signal and remove noise from the rectified echo ultrasound signal. The image processor 400 may obtain ultrasound image information from the object using the echo ultrasound signal processed as described above.

The controller 500 may generate various types of ultrasound images by receiving ultrasound image information from the image processor 400. In accordance with an embodiment, the various types of ultrasound images generated by the controller 500 may include an amplitude-mode (A-mode) image, a brightness-mode (B-mode) image, a motion-mode (M-mode) image, and a Doppler-mode image.

Also, the controller 500 may receive various information from a user via the user input unit 150. Also, the controller 500 may store information input via the user input unit 150 in the storage unit 600 and control ultrasound image information obtained from the image processor 400 to be output to the user interface unit 900. Also, the controller 500 may transmit various information to or receive various information from the communication unit 700.

In detail, the controller 500 may divide image information of an object in units of regions of a human body, based on image information obtained from the image processor 400.

In this case, the controller 500 may divide the image information in units of the regions of the human body included in an ultrasound image using at least one among a line, a plane, and a color, based on the image information obtained from the image processor 400. Thus, a user may figure out the image information of the object, which is output to the user input unit, at once by viewing a screen divided in units of the regions of the human body.

When a portion of the image information divided in units of the regions of the human body is selected via the user input unit 150, the controller 500 may increase or decrease the size of the portion.

The controller 500 may divide image information obtained from the image processor 400 into at least one among images of a bone, a blood vessel, a nerve, a muscle, and a ligament of an object (when it is assumed that the object is an arm). Alternatively, the controller 500 may divide the image information obtained from the image processor 400 into at least one among images of a blood vessel, a nerve, and some tissues of an object (when it is assumed that the object is an internal organ of a human body, e.g., a liver).

Also, the controller 500 may extract skeleton information from ultrasound image information of an object received via the image processor 400. Also, the controller 500 may generate a body marker of a model of a human body of an object (a portion to be diagnosed) of an examinee, based on the extracted skeleton information and location information of the ultrasound probe 200.

Here, the location information of the ultrasound probe 200 may be understood to include a relative position of the ultrasound probe 200 in an image of the object, an identification mark representing the location of the ultrasound probe 200, coordinate information of the location of the ultrasound probe 200, etc.

Also, the controller 500 may clearly express an object by generating a body marker of a model of a human body from an actual image of an object using the ultrasound probe 200 as described above. Also, the controller 500 may store the generated body marker in the storage unit 600.

Also, the controller 500 may generate a body marker in the form of at least one among a cross-sectional image, a 2D image, a 3D image, and a four-dimensional (4D) image.

Also, although the controller 500 may generate a body marker based on an ultrasound image of an object as described above, it may instead use a body marker 601 representing the shape of each of region of a human body previously stored in the storage unit 600.

Thus, the controller 500 may read out the previously stored body marker 601 representing the shape of each of the regions of the human body from the storage unit 600. Also, the controller 500 may compare an image of the object with the previously stored body marker 601 of a model of the human body.

Also, the controller 500 may divide ultrasound image information, which is received from the image processor 400, in units of regions of a human body according to an anatomical classification criterion as described above, and map body markers corresponding to the regions of the human body to the ultrasound image information divided in units of the regions of a human body. In this case, the body markers may include a plurality of layers or one layer according to a region of the human body.

In this case, the mapped body markers may include at least one among a body marker generated by the controller 500 and the body marker 601 corresponding to each of the regions of the human body and previously stored in the storage unit 600 as described above. Similarly, the body marker 601 may include a plurality of body markers or one layer according to the regions of the human body.

Also, the controller 500 may receive diagnostic history information, treatment schedule information, diagnostic information, reference information, reference image information, reference annotation information, etc. of a patient from a server or the Internet via the communication unit 700, and store the received information in the storage unit 600.

Also, the controller 500 may modify various information input to either a generated body marker of each of regions of a human body or the body marker 601 of each of the regions of the human body stored in the storage unit 600. In this case, the body marker for each of the regions of the human body may include a plurality of layers as described above.

The storage unit 600 may store a program for processing and controlling functions performed by the controller 500 and perform a function of temporarily storing input/output data. Also, the storage unit 600 may store various information processed by the ultrasound imaging apparatus. The storage unit 600 may be embodied as various types of storage media, e.g., a flash memory, a hard disc, an EEPROM, etc. Alternatively, the ultrasound imaging apparatus may manage a web storage or a cloud server configured to perform a storing function of the storage unit 600 on a web.

Also, the storage unit 600 may store medical data related to diagnosing an object, e.g., input/output ultrasound data, ultrasound images, etc., and store an algorithm or a program performed in the ultrasound imaging apparatus.

Also, the storage unit 600 may store information regarding a body marker generated by the controller 500. In addition, the body marker 601 of each of the regions of the human body may have been previously stored in the storage unit 600.

The communication unit 700 may include at least one element for communicating with an external device, e.g., a local-area communication module, a wire communication module, and a mobile communication module.

The local-area communication module means a module for establishing local-area communication within a predetermined distance. Examples of a local-area communication technology in accordance with an embodiment of the present invention may include, but are not limited to, a wireless local area network (LAN), Wi-Fi, Bluetooth, Zigbee, Wi-Fi direct (WFD), an ultra wideband (UWB), infrared data association (IrDA), Bluetooth low energy (BLE), near-field communication (NFC), etc.

The wire communication module means a module for establishing communication using an electrical signal or an optical signal. Examples of a wire communication technology in accordance with an embodiment of the present invention may include a pair cable, a coaxial cable, an optical cable, an Ethernet cable, etc.

The mobile communication module is configured to exchange a radio signal with at least one among a base station, an external terminal, and a server in a mobile communication network. Here, examples of the radio signal may include a voice call signal, a video call signal, and various types of data generated by exchanging texts/multimedia messages. The communication unit 700 may communicate with the controller 500 in the ultrasound imaging apparatus.

Also, the communication unit 700 may communicate with the controller 500 with data obtained from a hospital server connected to the communication unit 700 via a picture archiving and communication system (PACS) or another medical apparatus connected to the communication unit 700 in a hospital via the PACS.

Also, the communication unit 700 may establish data communication with the controller 500 according to the Digital Imaging and Communications in Medicine (DICOM) standard.

Also, the communication unit 700 may exchange data related to diagnosing an object, e.g., an ultrasound image, ultrasound data, Doppler data, etc., with the controller 500 via a network in the ultrasound imaging apparatus and may also exchange medical images captured using other medical apparatuses such as a CT, an MRI, an X-ray, etc., with the controller 500.

Furthermore, the communication unit 700 may receive a diagnostic history, a treatment schedule, diagnostic information, reference information, reference image information, reference annotation information of a patient, etc. from a server or the Internet and transmit the received information to the controller 500.

Also, the communication unit 700 may establish data communication with not only a server or medical apparatuses installed in a hospital but also a portable terminal belonging to a doctor or a patient.

The user interface unit 900 means a device configured to help an interaction between a user and the controller 500 to smoothly occur.

The user interface unit 900 may include the display unit 160 and the sub-display unit 161 which are configured to display various UIs related to controlling an ultrasound apparatus.

The user interface unit 900 may output an ultrasound image of an object via the display unit 160 or the sub-display unit 161.

Also, the user interface unit 900 may be configured to check various UIs provided via the controller 500 and input various commands for the controller 500 via the display unit 160 or the sub-display unit 161 using a touch screen.

Hereinafter, it is assumed that an output of the user interface unit 900 is output via the display unit 160 or the sub-display unit 161.

The user interface unit 900 may output pieces of image information of an ultrasound image divided in units of regions of a human body and a body marker mapped to the image information. In this case, the body marker may include a plurality of layers.

The user interface unit 900 may output the body marker in the form of at least one among a 2D image, a 3D image, and a 4D image.

The functions of the ultrasound imaging apparatus in accordance with an embodiment of the present invention have been described above with respect to the elements of the ultrasound imaging apparatus.

A process of obtaining and mapping an ultrasound image performed by an ultrasound imaging apparatus, in accordance with an embodiment of the present invention will be described with reference to FIGS. 3 to 7 below.

FIG. 3 is a flowchart of a process of outputting a body marker using an ultrasound imaging apparatus in accordance with one embodiment of the present invention.

Referring to FIGS. 2 and 3, a user may obtain ultrasound image information regarding an object via the beam forming unit 300 and the image processor 400 by placing the ultrasound probe 200 to be in contact with a region of a human body to be diagnosed (operation S1000).

In detail, the image processor 400 may obtain the ultrasound image information regarding the object using the ultrasound probe 200. Also, the image processor 400 may obtain location information of the ultrasound probe 200.

For example, the image processor 400 may obtain information regarding a location on an examinee on which the ultrasound probe 200 is placed using various sensors, a video camera, etc. included in the ultrasound probe 200.

The image processor 400 may transmit to the controller 500 the ultrasound image information regarding the object corresponding to the location information obtained using the ultrasound probe 200. For example, when the ultrasound probe 200 is located on the head of an examinee, the image processor 400 may obtain image information regarding a brain as an object corresponding to the location information of the ultrasound probe 200.

When the ultrasound probe 200 is located on a left chest of an examinee, the image processor 400 may obtain image information regarding a heart as an object corresponding to the location information of the ultrasound probe 200.

The controller 500 of the ultrasound imaging apparatus may generate an ultrasound image based on the ultrasound image information received from the image processor 400. Information regarding the generated ultrasound image may be divided in units of regions of a human body according to an anatomical classification criterion (operation S1010), as will be described in detail with reference to FIGS. 4A and 4B below.

Figure 4A:
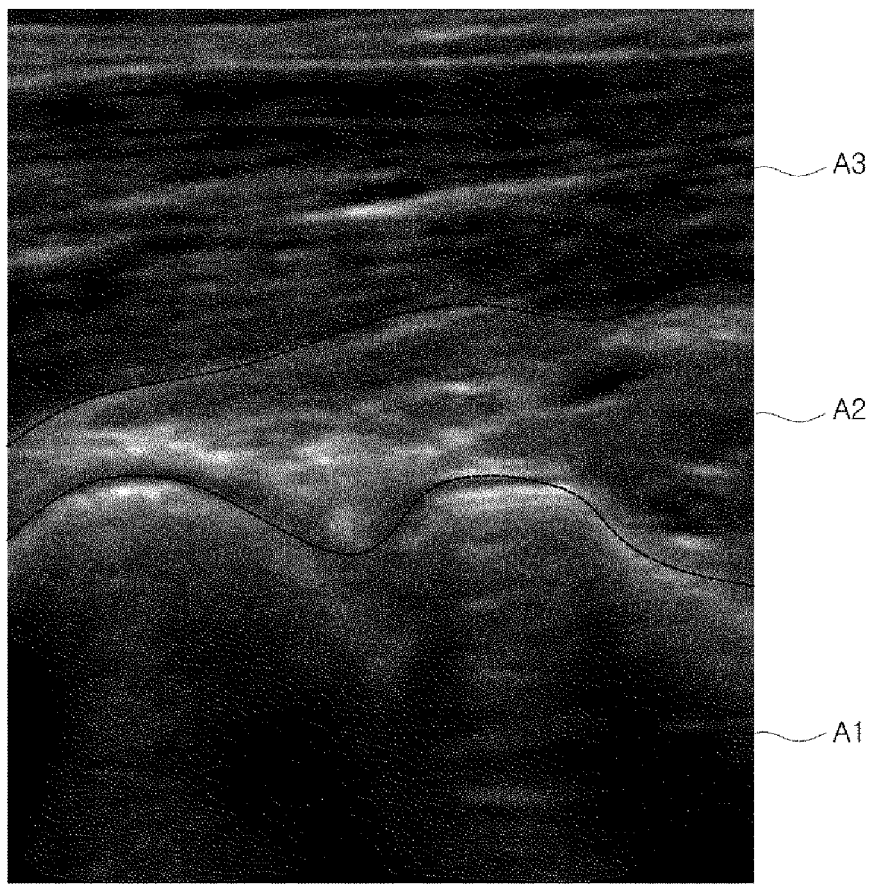
FIG. 4A illustrates an ultrasound image of a portion of a human body.
Figure 4B:
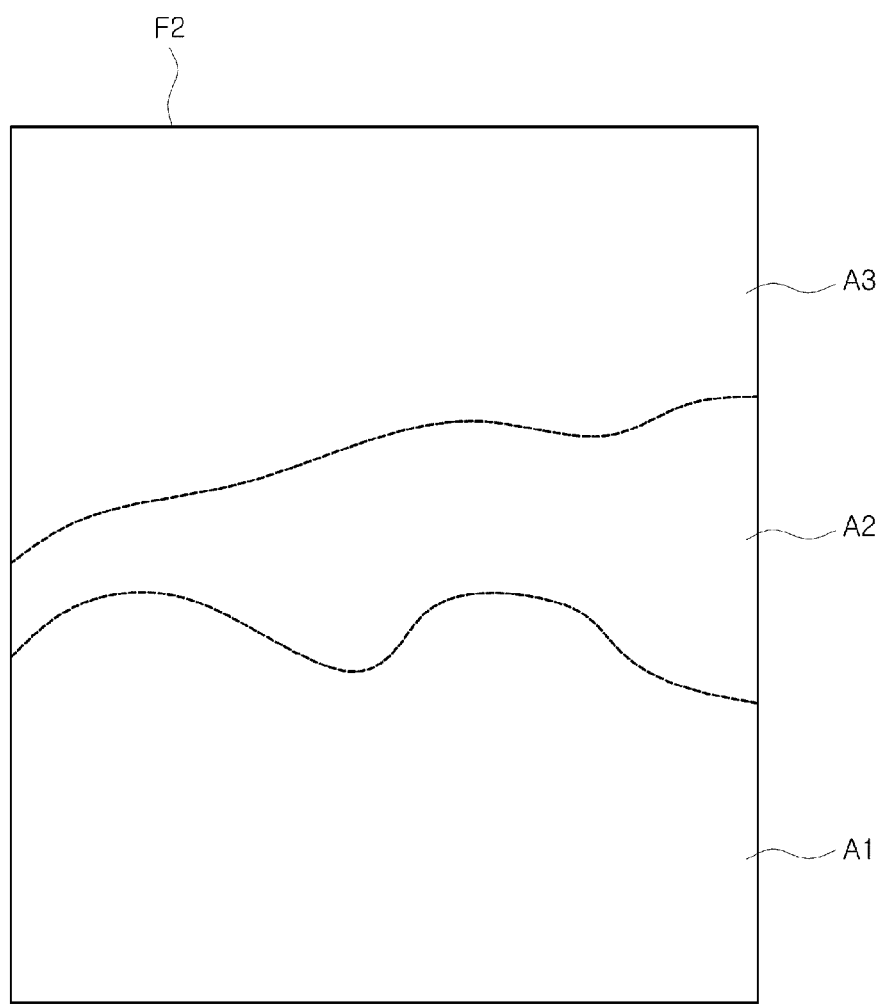
FIG. 4B is a diagram of the ultrasound image of FIG. 4A divided by lines, such that regions of the human body are easily recognizable.

FIG. 4A illustrates an object (a region of a body to be diagnosed) of an examinee, and particularly, an ultrasound image F2 of a right elbow of the examinee. FIG. 4B illustrates regions of the body of the examinee in the ultrasound image F2 of the right elbow illustrated in FIG. 4A, divided by lines.

In FIGS. 4A and 4B, it is assumed that a first region A1 and a second region A2 respectively represent a bone and a nerve of the object (i.e., the elbow of the examinee).

Also, it is assumed that a third region A3 represents a muscle of the object (i.e., the elbow of the examinee).

For example, the controller 500 may divide ultrasound image information, which is received from the image processor 400, according to an anatomical classification criterion. Thus, the ultrasound image F2 of the right elbow may be divided into a bone region, a nerve region, and a muscle region by dividing the ultrasound image F2 into the first to third regions A1 to A3.

In this case, the controller 500 may divide the ultrasound image F2 of the right elbow into the first to third regions A1 to A3, and divide the bone region (the first region A1), the nerve region (the second region A2), and the muscle region (the third region A3) into planes (see FIG. 4A). Alternatively, the controller 500 may divide the ultrasound image F2 of the right elbow into the first region A1 to the third region A3, and divide the bone region (the first region A1), the nerve region (the second region A2), and the muscle region (the third region A3) using lines (see FIG. 4B).

Figure 5A:
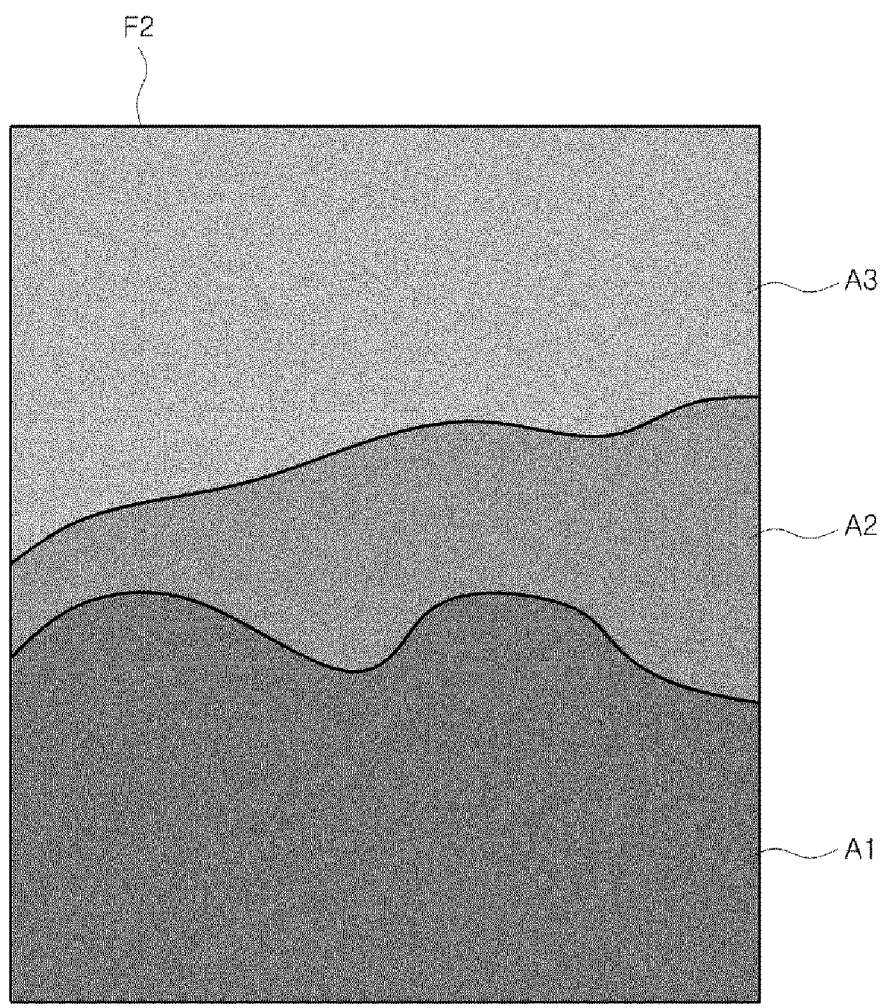
FIG. 5A is a diagram illustrating a result of displaying regions of a human body included in an ultrasound image using different colors.

FIG. 5A is a diagram illustrating a result of displaying regions of a human body included in an ultrasound image using different colors.

The controller 500 may divide an ultrasound image F2 of a right elbow of an examinee into first to third regions A1 to A3, and distinguish a bone region (the first region A1), a nerve region (the second region A2), and a muscle region (the third region A3) using different colors (see FIG. 5A). Although in FIG. 5A, these regions are in units of shades of black and white, exemplary embodiments of the present invention are not limited thereto and the first region A1 to the third region A3 may be divided using different colors.

Thus, a user may figure out a plurality of pieces of image information of an ultrasound image divided in units of regions of a human body at a time using a line, a plane, a color, etc.

Figure 5B:
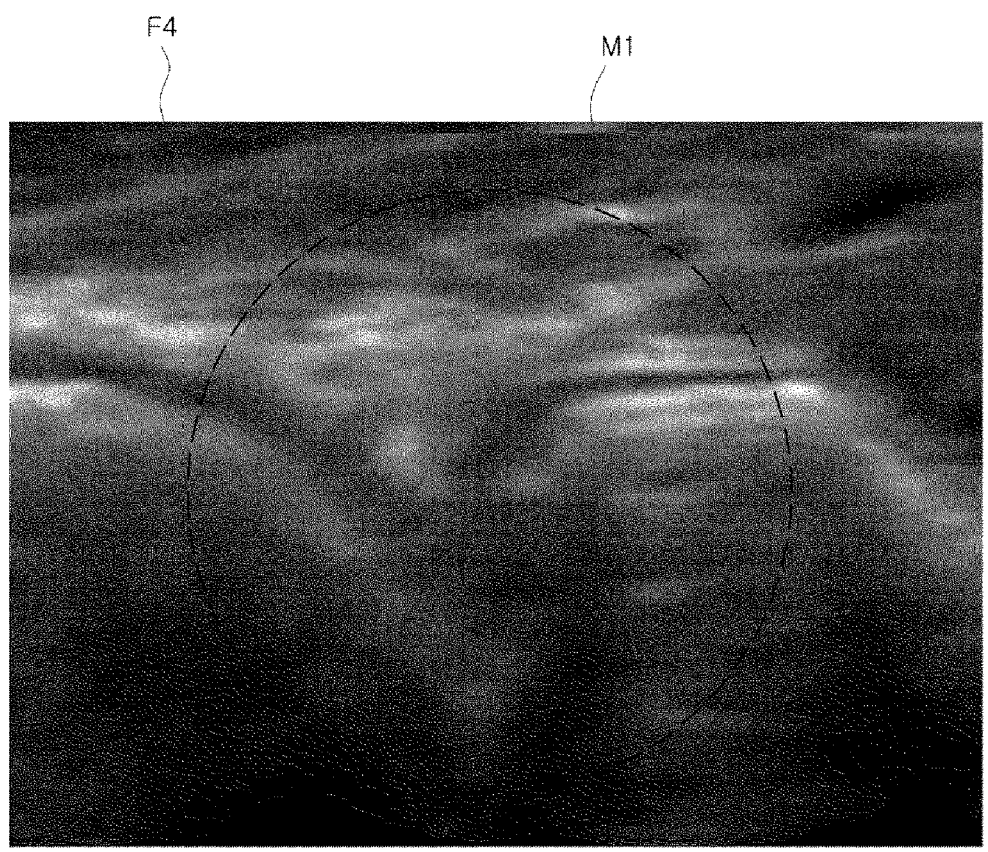
FIG. 5B illustrates a result of expanding one of regions of a human body included in an ultrasound image.

FIG. 5B illustrates an ultrasound image F4 which is a result of expanding one of region of a human body included in an ultrasound image. The ultrasound image F4 is a result of expanding a portion having a corrugated shape M1 of the bone of the elbow which is the first region A1 of FIG. 4A.

When one of a plurality of pieces of image information divided in units of the regions of the human body is selected via the user input unit 150 or the user interface unit 900, the controller 500 may increase or decrease the size of the selected image information. Thus, a user may minutely observe the regions of the human body included in the ultrasound image.

Figure 6:
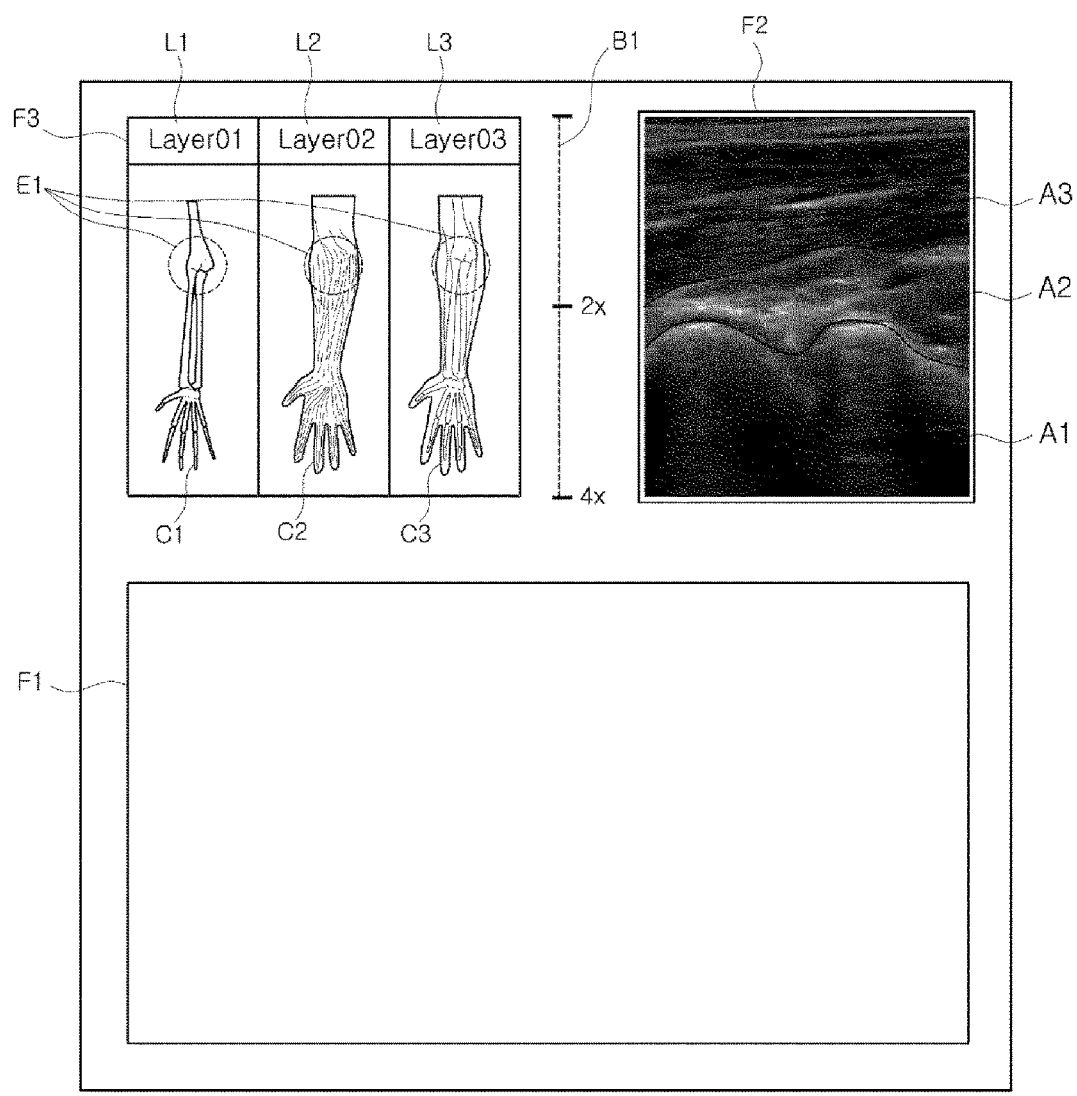
FIG. 6 is a diagram illustrating an ultrasound image of a region of a human body and a body marker corresponding thereto.
Figure 7:
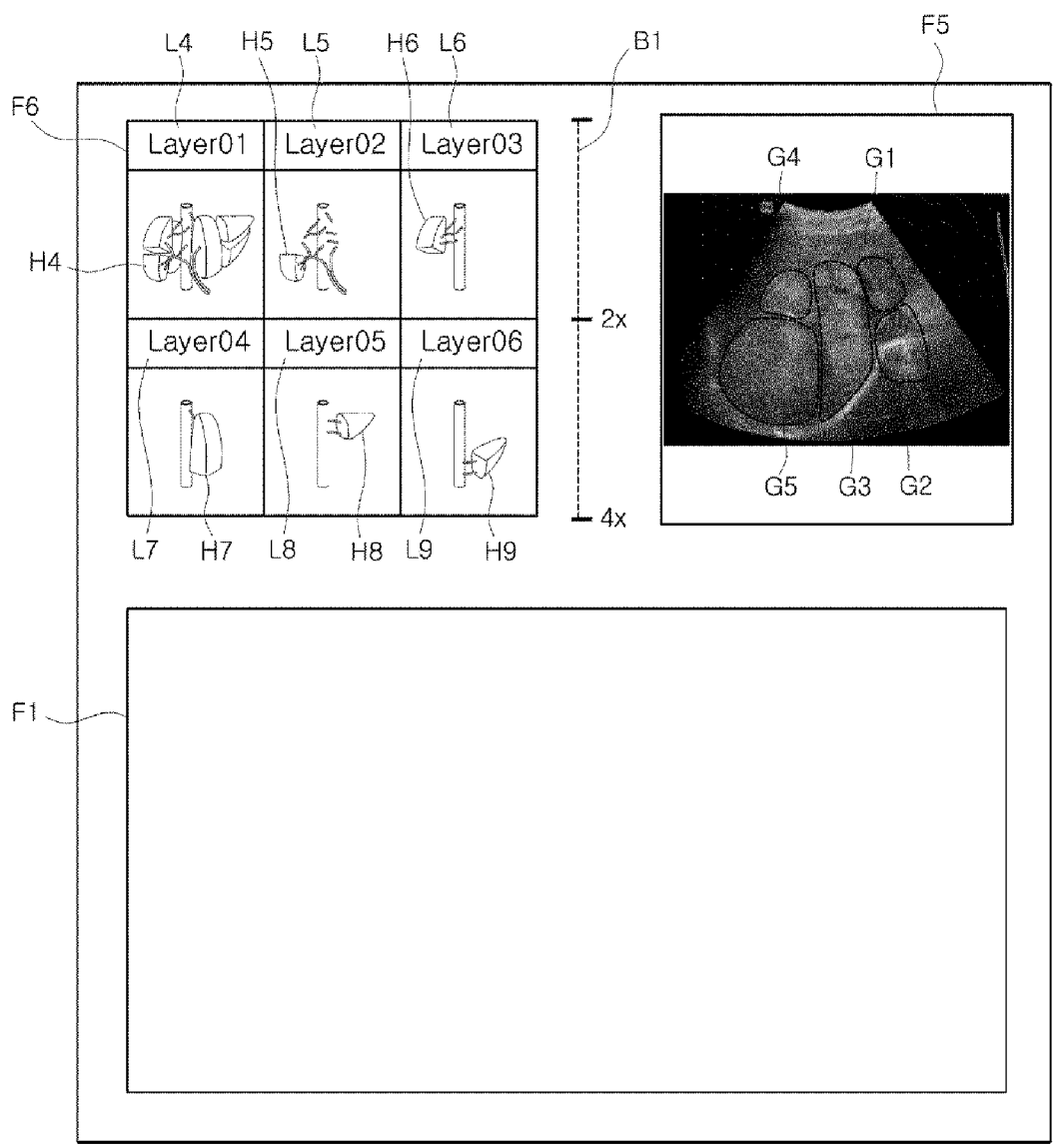
FIG. 7 is a diagram illustrating an ultrasound image of an internal organ of a human body and a body marker corresponding thereto.

FIG. 6 is a diagram illustrating an ultrasound image of a region of a human body and a body marker corresponding to the region. FIG. 7 is a diagram illustrating an ultrasound image of an internal organ of a human body and a body marker corresponding to the internal organ.

The controller 500 may generate an ultrasound image based on ultrasound image information received from the image processor 400. Also, the controller 500 may divide the generated ultrasound image in units of regions of a human body of an object, and generate a body marker of a model of a human body corresponding to each of the regions of the human body.

In this case, the controller 500 may map the generated body marker to a region of an ultrasound image of the human body. (operation S1020). Alternatively, the controller 500 may map to the region of the human body the body marker 601 of a model of a human body, previously stored in the storage unit 600 (operation S1020).

Alternatively, the controller 500 may output body markers for respective regions of the human body corresponding to images of the ultrasound image divided in units of the regions of the human body.

In detail, the ultrasound image F2 of FIG. 6 which is an upper right portion of a screen displayed on the user interface unit 900 may be an ultrasound image of a right elbow of the object.

A lower screen F1 which is a lower portion of the screen displayed on the user interface unit 900 will be described in detail with reference to FIGS. 9 to 14 below.

In the ultrasound image F2 which is the upper right portion of the screen, the first region A1 of the human body represents the bone of the right elbow, the second region A2 represents the nerve of the right elbow, and the third region A3 represents the muscle of the right elbow.

However, the present invention is not limited thereto, and the first to third regions A1 to A3 may represent skin, tissue, etc. of the right elbow other than bone, ligament, nerve, and muscle of the right elbow.

The controller 500 may generate a body marker of a model of a human body corresponding to the first region A1 to the third region A3 of the human body. In this case, body markers C1 to C3 respectively including a plurality of layers L1 to L3 may be generated to correspond to a plurality of images.

In detail, the body marker C1 of the first layer L1 generated by the controller 500 represents a bone of a right elbow portion E1. The controller 500 may map the body marker C1 of the first layer L1 to the first region A1 representing the bone of the right elbow in the ultrasound image information F2.

The body marker C2 of the second layer L2 generated by the controller 500 represents a nerve of the right elbow portion E1. The controller 500 may map the body marker C2 of the second layer L2 to the second region A2 representing the nerve in the ultrasound image information F2.

The body marker C3 of the third layer L3 generated by the controller 500 represents a muscle of the right elbow portion E1. The controller 500 may map the body marker C3 of the third layer L3 to the third region A3 representing the muscle in the ultrasound image information F2.

Also, the controller 500 may output a body marker for each of the regions of the human body mapped to images of the above ultrasound image divided in units of the regions of the human body (operation S1030), as will be described in detail with reference to FIGS. 9 to 14 below.

A dotted line B1 at the middle of the screen displayed on the user interface unit 900 represents an expansion or reduction rate. Thus, the controller 500 may increase or decrease the ultrasound image F2 by adjusting the dotted line according to an input received via the user input unit 150 or the user interface unit 900.

As another example, a liver which is an internal organ of a human body will be described in detail with reference to FIG. 7 below.

An ultrasound image F5 which is an upper right portion of a screen displayed on the user interface unit 900 may be an ultrasound image of a liver which is an internal organ of a human body.

A screen F6 which is an upper left portion of the screen displayed on the user interface unit 900 represents body markers H4 to H9 of a model of an internal organ, e.g., a liver, of a human body including a plurality of layers L4 to L9 corresponding to regions of the internal organ.

A lower screen F1 below the screen displayed on the user interface unit 900 will be described in detail with reference to FIGS. 9 to 14 below.

In an ultrasound image F5 which is an upper right portion of the screen displayed on the user interface unit 900, a first region G1, a second region G2, and a third region G3 of the internal organ (e.g., the liver) respectively represent an upper right lobe, a lower right lobe, and a middle lobe of the internal organ (e.g., the liver).

A fourth region G4 and a fifth region G5 of the internal organ (e.g., the liver) respectively represent an upper left lobe and a lower left lobe of the internal organ (e.g., the liver).

However, the first to fifth regions G1 to G5 are merely examples and may represent other portions of the liver, and thus the present invention is not limited thereto.

The controller 500 may generate a body marker of a model of the internal organ (e.g., the liver) of the human body corresponding to the first to fifth regions G1 to G5 of the internal organ, e.g., the liver, of the human body. In this case, body markers H4 to H9 respectively including a plurality of layers L4 to L9 corresponding to a plurality of images may be generated.

In detail, the body marker H4 of the first layer L4 generated by the controller 500 represents a whole model of the internal organ (e.g., the liver) of the human body. Also, the controller 500 may map the body marker H4 of the first layer L4 to all of the regions G1 to G5 representing the liver which is the internal organ in the ultrasound image information F5.

The body marker H5 of the second layer L5 generated by the controller 500 represents the lower left lobe of the internal organ (e.g., the liver). The controller 500 may map the body marker H5 of the second layer L5 to the fifth region G5 representing the lower left lobe of the liver which is the organ of the human body in the ultrasound image information F5.

The body marker H6 of the third layer L6 generated by the controller 500 represents the upper left lobe of the internal organ (e.g., the lobe) of the human body. The controller 500 may map the body marker H6 of the third layer L6 to the fourth region G4 representing the upper left lobe of the liver which is an internal organ of the human body in the ultrasound image information F5.

The body marker H7 of the fourth layer L7 generated by the controller 500 represents the upper right lobe of the internal organ (e.g., the liver) of the human body. The controller 500 may map the body marker H7 of the fourth layer L7 to the first region G1 representing the upper right lobe of the liver which is an internal organ of the human body in the ultrasound image information F5.

The body marker H7 of the fourth layer L7 generated by the controller 500 represents the middle lobe of the internal organ (e.g., the liver) of the human body. The controller 500 may map the body marker H7 of the fourth layer L7 to the third region G3 representing the middle lobe of the liver which is an internal organ of the human body in the ultrasound image information F5.

The body marker H8 of the fifth layer L8 generated by the controller 500 represents the upper right lobe of the internal organ (e.g., the liver) of the human body. The controller 500 may map the body marker H8 of the fifth layer L8 to the first region G1 representing the upper right lobe of the liver which is an internal organ of the human body in the ultrasound image information F5.

The body marker H9 of the sixth layer L9 generated by the controller 500 represents the lower right lobe of the internal organ (e.g., the liver) of the human body. The controller 500 may map the body marker H9 of the sixth layer L9 to the second region G2 representing the lower right lobe of the liver which is an internal organ of the human body in the ultrasound image information F5.

A dotted line B1 at a middle of the screen displayed on the user interface unit 900 represents an expansion or reduction rate. Thus, the controller 500 may increase or decrease the size of the ultrasound image F2 by adjusting the dotted line B1 according to an input received via the user input unit 150 or the user interface unit 900.

A process of dividing an ultrasound image in units of regions of a human body and mapping a body marker of a model of the human body to each of the regions of the human body, which is performed by an ultrasound imaging apparatus, has been described above.

A process of writing information to or modifying information in a body marker corresponding to an ultrasound image divided in units of regions of a human body, which is performed by a user, will now be described in detail with reference to FIGS. 8 to 14.

Figure 8:
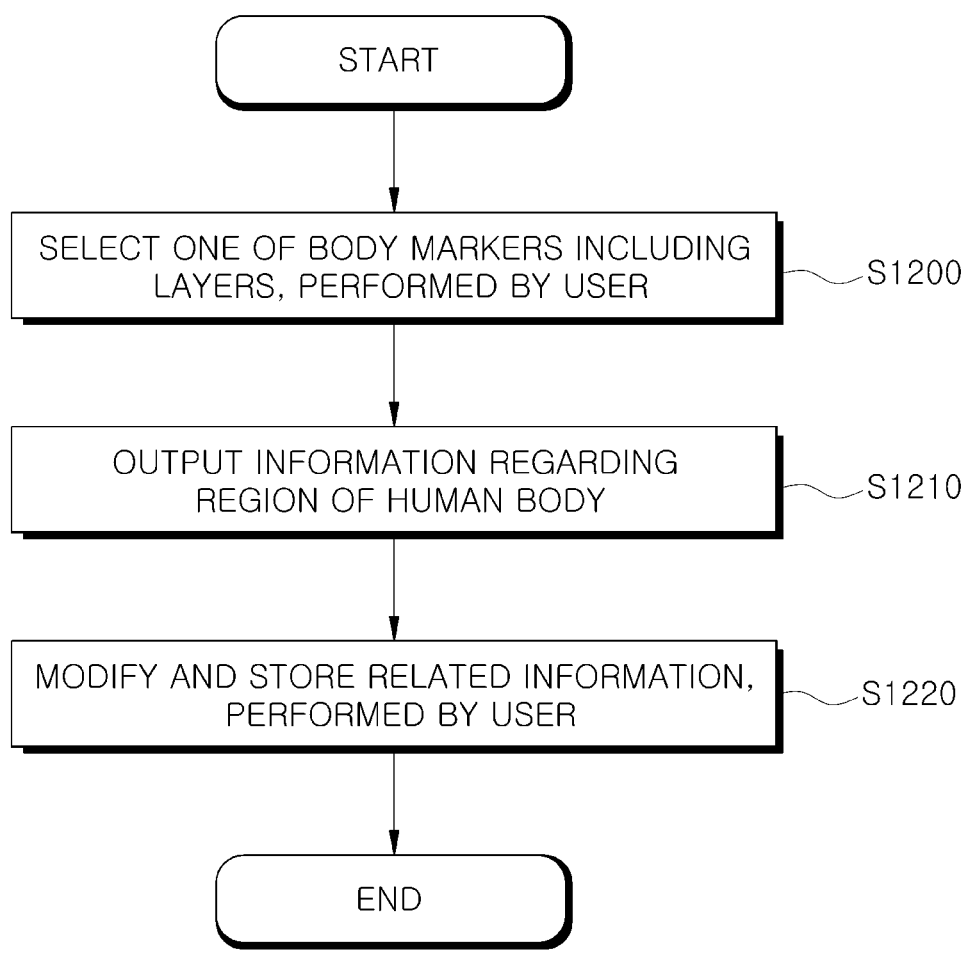
FIG. 8 is a flowchart of a process of storing information in a body marker including a plurality of layers in accordance with an embodiment of the present invention.

FIG. 8 is a flowchart of a process of storing information in a body marker including a plurality of layers in accordance with an embodiment of the present invention.

Figure 9:
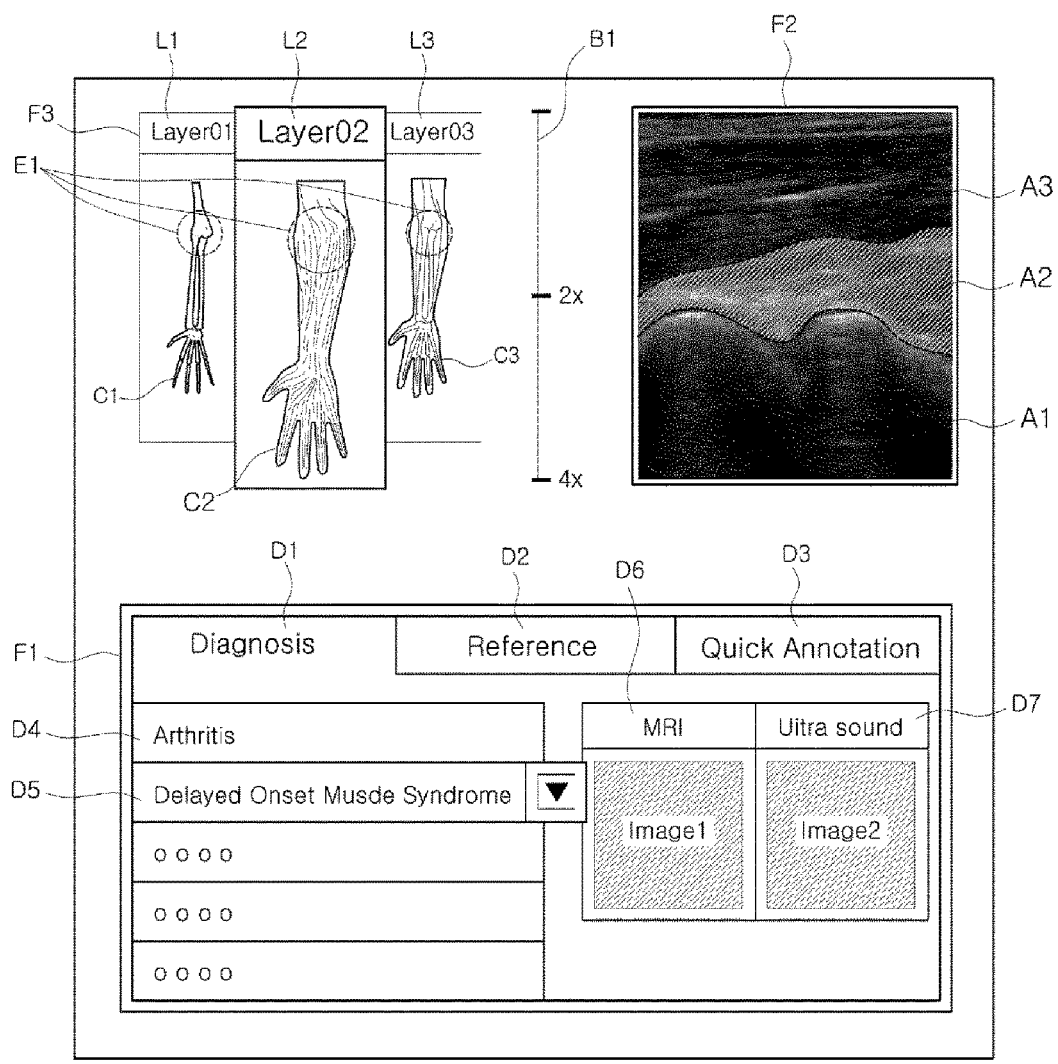
FIG. 9 illustrates a screen displaying a body marker mapped when a user selects one of a plurality of body markers and reference diagnostic information related to the body marker.
Figure 10:
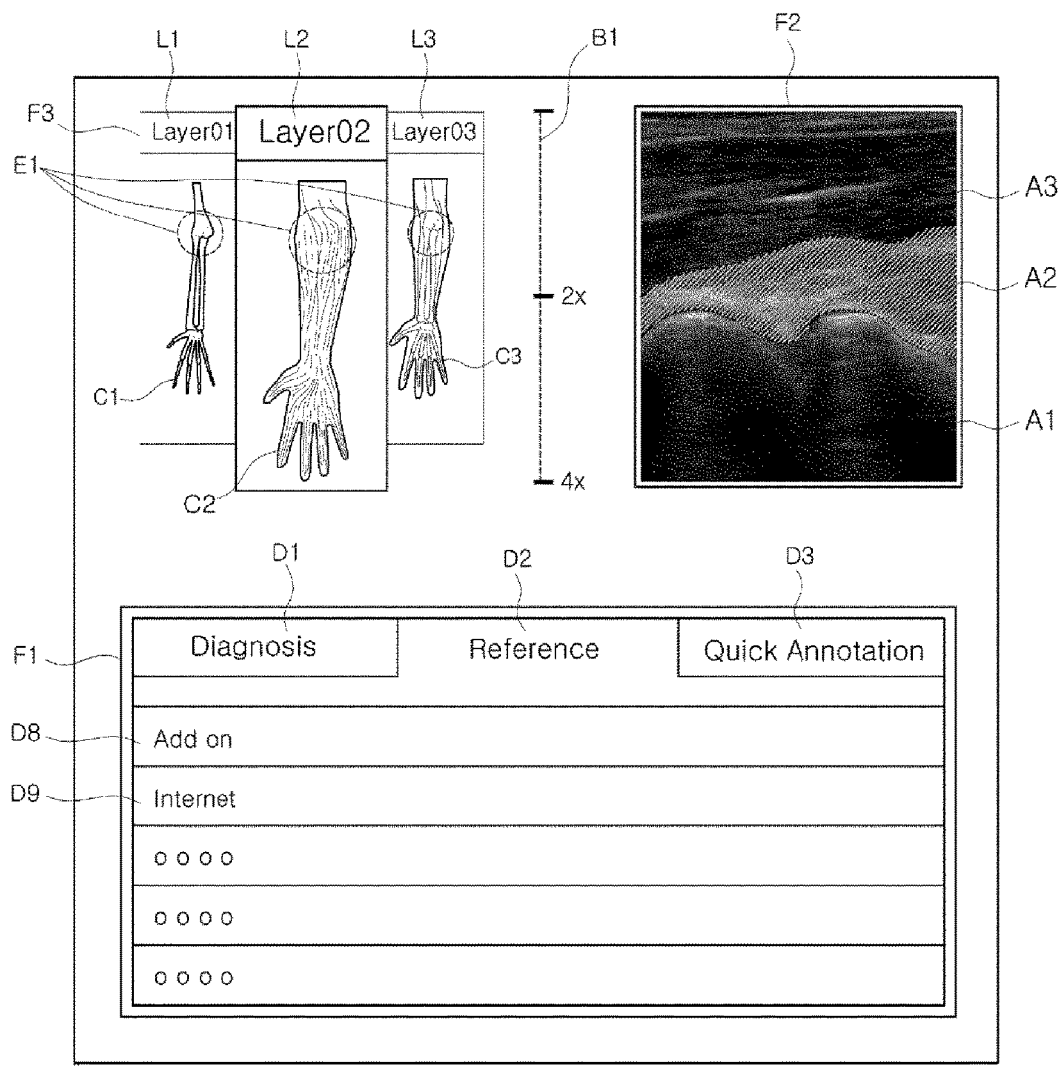
FIG. 10 illustrates a screen displaying a body marker mapped when a user selects one of a plurality of body markers and reference information related to the body marker.
Figure 11:
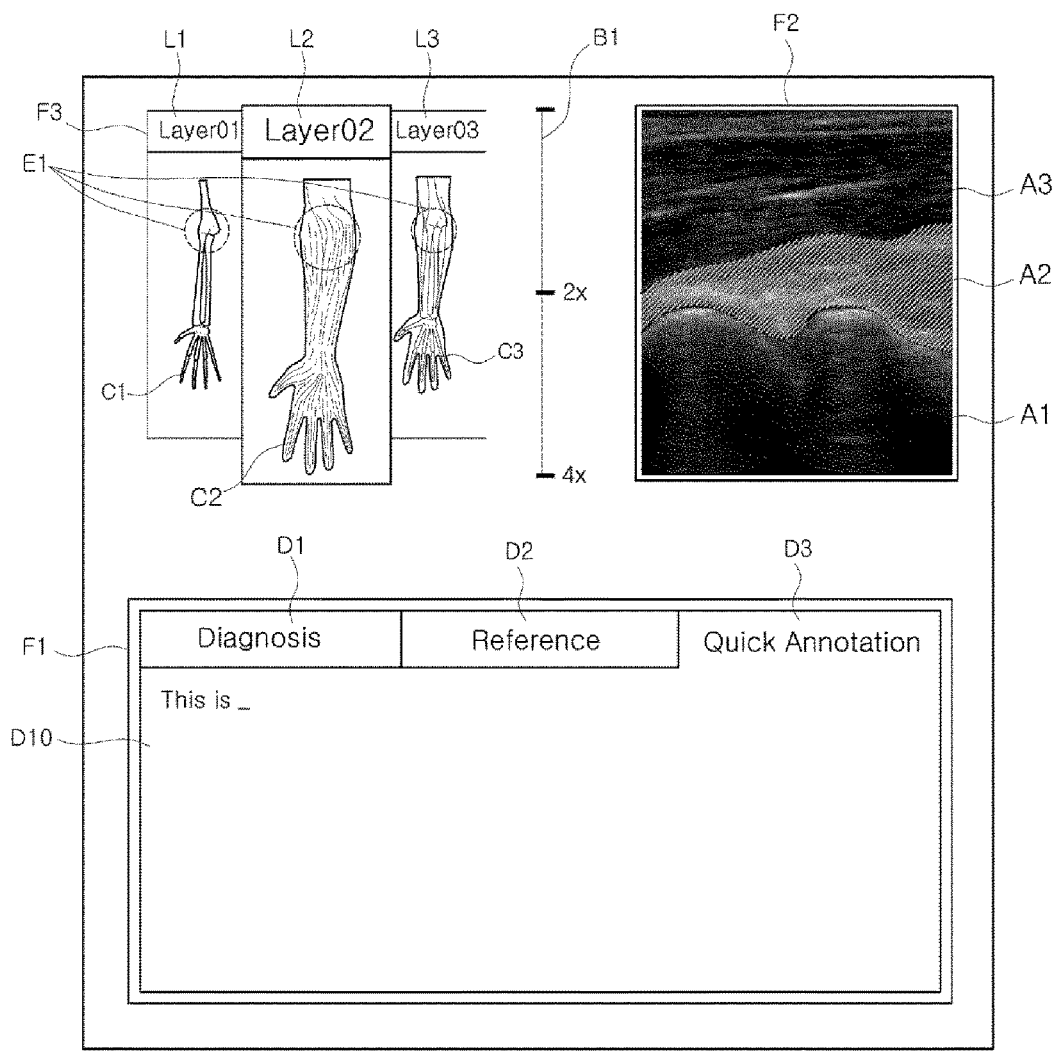
FIG. 11 illustrates a screen displaying a body marker mapped when a user selects one of a plurality of body markers and reference annotation information related to the body marker.

FIGS. 9 to 11 are diagrams illustrating processes of writing information to or modifying information in a body marker including a plurality of layers with respect to a right elbow of a human body in accordance with embodiments of the present invention.

A user may select one of body markers C1 to C3 respectively including a plurality of layers L1 to L3, for example, by touching the user input unit 150 or the user interface unit 900 in an output screen F3 displayed on the user interface unit 900 (operation S1200).

Also the user may select one of regions A1 to A3 of a human body included in an ultrasound image F2.

For example, when a user selects the body marker C2 of the second layer L2, for example, by touching the user input unit 150 or the user interface unit 900, a second region A2 of the ultrasound image F2 representing a nerve of a right elbow corresponding to the body marker C2 is mapped by the controller 500 and displayed using a line, a plane, a color, etc.

In contrast, when the user selects the second region A2 of the ultrasound image F2 representing the nerve of the right elbow, for example, by touching the user input unit 150 or the user interface unit 900, the body marker C2 of the second layer L2 corresponding to the second region A2 is mapped by the controller 500 and output similarly to an upper left screen F3. Thus, the user may easily figure out image information corresponding to each of regions of a human body.

Thus, when the user selects one of the second region A2 of the ultrasound image and the body marker C2 of the second layer L2 which represent the nerve of the right elbow, for example, by touching the user input unit 150 or the user interface unit 900, information F1 related to a region of the human body corresponding to the selected second region A1 or the body marker C2 is output (operation S1210).

In detail, in a lower screen F1 which is a lower screen among the screens displayed on the user interface unit 900, diagnostic information D1, reference information D2, and reference annotation information (quick annotation) D3 regarding the nerve of the right elbow are output.

The user may select the diagnostic information D1, the reference information D2, or the reference annotation information (quick annotation) D3, for example, by touching the user input unit 150 or the user interface unit 900.

Here, when the user selects the diagnostic information D1 as illustrated in FIG. 9, information such as a name D4 and a symptom D5 of a disease, an MRI reference image D6, an ultrasound photograph D7 of the right elbow, etc. are output.

As illustrated in FIG. 10, the user may select the reference information D2 and, for example, touch the user input unit 150 or the user interface unit 900 to add or modify related material information, an MRI reference image, an ultrasound photograph, etc. (D8) (operation S1220).

In addition, the user may communicate with an external device and the Internet D9 via the communication unit 700 to download, add, or modify related material information, an MRI reference image, an ultrasound photograph, etc.

Also, as illustrated in FIG. 11, the user may select the reference annotation information (quick annotation) D3 and, for example, touch the user input unit 150 or the user interface unit 900 to write annotation information regarding the name and symptom of the disease, an MRI reference image, an ultrasound image, etc. (D10).

In addition, the user may communicate with an external device and the Internet D9 via the communication unit 700 to download, add, or modify related material information, an MRI reference image, an ultrasound photograph, etc.

As another example, a liver which is an internal organ of a human body will be described in detail with reference to FIGS. 12 to 14 below.

Figure 12:
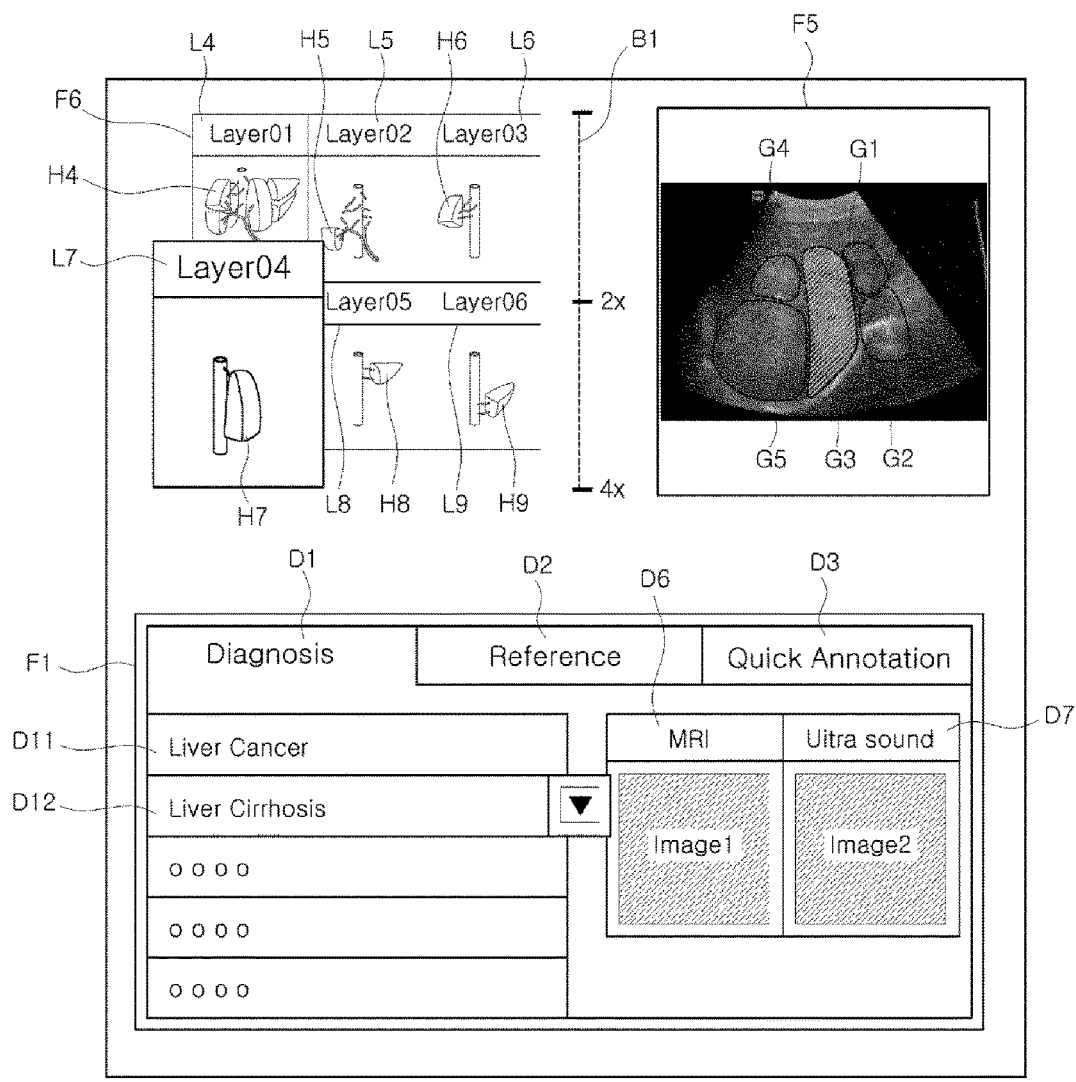
FIG. 12 illustrates a screen displaying a body marker mapped when a user selects one of a plurality of body markers and reference diagnostic information related to the body marker.
Figure 13:
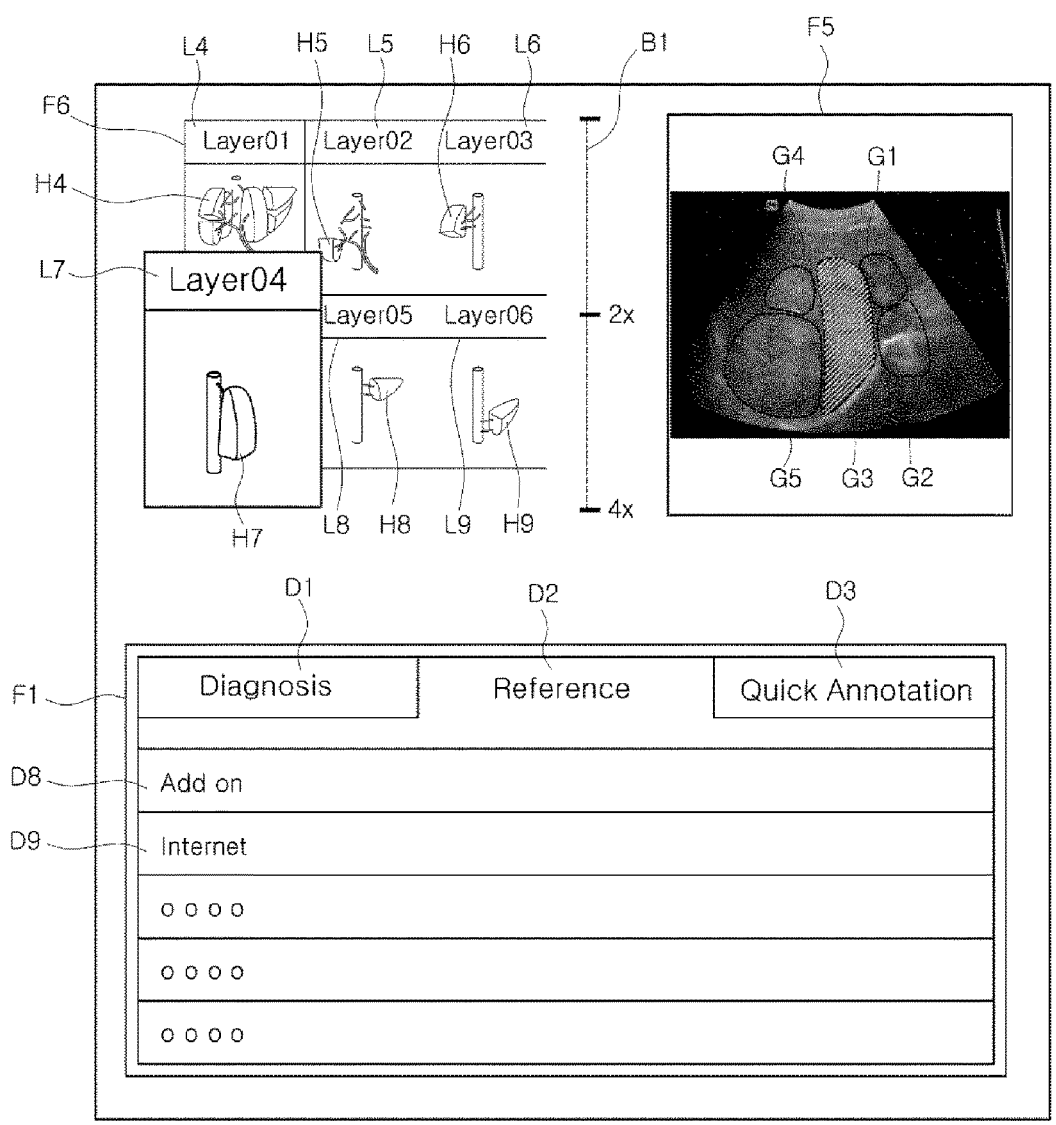
FIG. 13 illustrates a screen displaying a body marker mapped when a user selects one of a plurality of body markers and reference information related to the body marker.
Figure 14:
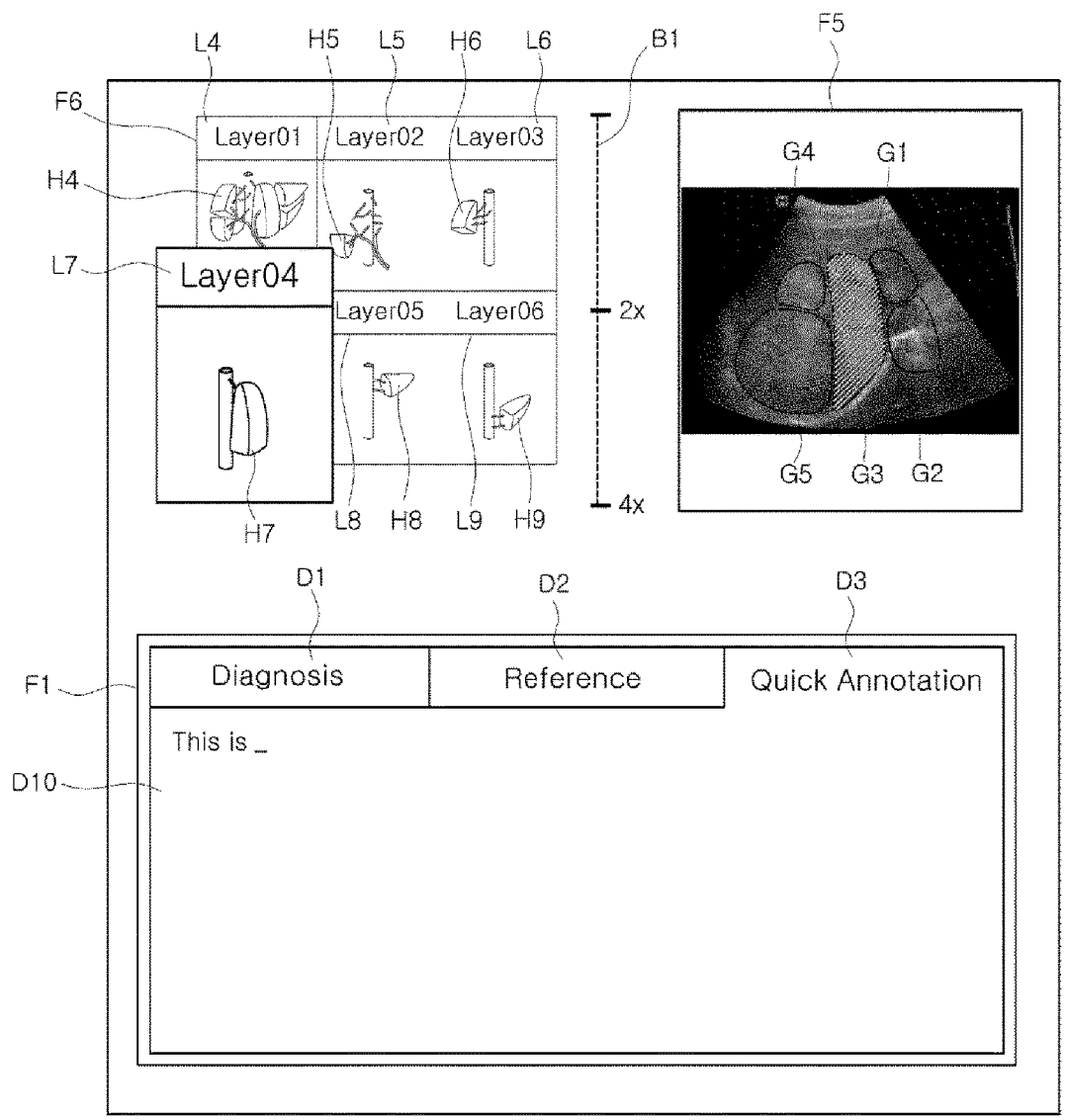
FIG. 14 illustrates a screen displaying a body marker mapped when a user selects one of a plurality of body markers and reference annotation information related to the body marker.

FIGS. 12 to 14 are diagrams illustrating processes of writing information to or modifying information in a body marker including a plurality of layers with respect to a liver which is an internal organ of a human body, according to other embodiments of the present invention.

A user may select one of body markers H4 to H9 respectively including a plurality of layers L4 to L9 in a screen F6 displayed on the user interface unit 900, for example, by touching the user input unit 150 or the user interface unit 900 (operation S1200).

Also, the user may select one of regions G1 to G5 of an ultrasound image F5 corresponding to portions of the liver which is an internal organ of the human body.

For example, when the user selects the body marker H7 of the fourth layer L7, for example, by touching the user input unit 150 or the user interface unit 900, the third region G3 of the ultrasound image F2 representing the middle lobe of the liver which is the internal organ of the human body and corresponding to the body marker H7 of the fourth layer L7 is mapped to the body marker H7 by the controller 500 and is output using a line, a plane, a color, etc.

In contrast, when the user selects the third region G3 of the ultrasound image F2 representing the middle lobe of the liver which is the internal organ of the human body, for example, by touching the user input unit 150 or the user interface unit 900, the body marker H7 of the fourth layer L7 corresponding to the third region G3 is mapped to the third region G3 by the controller 500 and is output similarly to a screen F3 which is an upper left screen. Thus, a user may easily figure out image information for each of the regions of the human body using these body markers.

When a user selects one of the third region G3 of the ultrasound image and the body marker H7 of the fourth layer L7 which represent the middle lobe of the liver which is the internal organ of the human body, for example, by touching the user input unit 150 or the user interface unit 900, information (F1) regarding the middle lobe of the liver and corresponding to the third region G3 or the body marker H7 is output (operation S1210).

In detail, in the screen F1 which is a lower screen among screens displayed on the user interface unit 900, diagnostic information D1, reference information D2, and reference annotation information (Quick Annotation) D3 related to the middle lobe of the liver which is an internal organ of the human body are output.

A user may select the diagnostic information D1, the reference information D2, and the reference annotation information (Quick Annotation) D3, for example, by touching the user input unit 150 or the user interface unit 900.

Here, when a user selects the diagnostic information D1 as illustrated in FIG. 12, information such as a name D11 and a symptom D12 of a disease of the middle lobe of the liver which is the internal organ of the human body D11, an MRI reference image D6, an ultrasound photograph D7, etc. is output.

Also, as illustrated in FIG. 13, a user may select the reference information D2, and add or modify related material information, an MRI reference image, an ultrasound photograph, etc., for example, by touching the user input unit 150 or the user interface unit 900 (D8) (operation S1220).

Furthermore, a user may communicate with an external device, the Internet, etc. (D9) via the communication unit 700 to download, add, or modify related material information, an MRI reference image, an ultrasound photograph, etc.

Also, as illustrated in FIG. 14, a user may select the reference annotation information (quick annotation) D3, and write annotation information such as the name and symptom of a disease, an MRI, an ultrasound image, etc. by, for example, touching the user input unit 150 or the user interface unit 900 (D10).

As is apparent from the above description, according to an ultrasound imaging apparatus and a method of controlling the same according to the one or more of the above embodiments of the present invention, a user may easily diagnose an object by easily figuring out an ultrasound image of the object obtained using an ultrasound probe, based on a body marker corresponding to the ultrasound image divided in units of regions of a human body.

According to an ultrasound imaging apparatus and a method of controlling the same according to the one or more of the above embodiments of the present invention, a user may add or modify diagnostic information, reference information, and reference annotation information in a body marker including a plurality of layers, thereby preventing an error between results of reading an ultrasound image, performed by a tester and a diagnostician.

According to an ultrasound imaging apparatus and a method of controlling the same according to the one or more of the above embodiments of the present invention, previous diagnostic information and present diagnostic information may be more precisely compared and determined based on information written to and stored in a body marker.

According to an ultrasound imaging apparatus and a method of controlling the same according to the one or more of the above embodiments of the present invention, a body marker is mapped to ultrasound images of regions of a human body so that a user may gain an intuition about a direction of a scan image and a region of the human body corresponding to the scan image.

An ultrasound imaging apparatus for obtaining an ultrasound image information, dividing the ultrasound image information in units of regions of a human body, mapping the ultrasound image information to a body marker, and storing or modifying related diagnostic information, reference information, and reference annotation information, and a method of controlling the same have been described above to particularly describe the present invention. However, the present is not limited thereto, and it would be apparent to those of ordinary skill in the art that the present invention may be modified or changed within the scope of the technical idea thereof.

A simple modification or change to the present invention should be construed as being in the scope of the present invention and the scope of the present invention should be defined by the appended claims.

The above methods of controlling an ultrasound imaging apparatus can be embodied as computer readable code in a computer readable medium. The computer readable medium may be any recording apparatus capable of storing data that is read by a computer system, e.g., a read-only memory (ROM), a random access memory (RAM), a magnetic tape, a magnetic disk, a flash memory, an optical data storage device, and so on. The computer readable medium can be distributed among computer systems that are interconnected through a computer communication network, and the present invention may be stored and implemented as computer readable code in the distributed system.

While the present invention has been particularly shown and described with reference to exemplary embodiments thereof, it will be understood by those of ordinary skill in the art that various changes in form and details may be made therein without departing from the spirit and scope of the invention as defined by the appended claims. The exemplary embodiments should be considered in descriptive sense only and not for purposes of limitation. For example, each component described as a single form may be divided and dispersed, and components described as being dispersed may be combined in a single form.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:
1. An ultrasound imaging apparatus comprising:
   an image processor configured to obtain image information from a transducer converting waves received from an object to electrical signals;
   a user interface unit comprising a display unit and configured to output by the display unit a result of mapping to the image information;

a controller communicatively connected to the image processor and user interface unit and configured to control the user interface unit, divide the obtained image information into pieces of image information in units of regions of a human body according to an anatomical classification criterion, and map a body marker to the pieces of image information based on at least one region of a bone, a blood vessel, a nerve, a muscle, and a ligament of the human body; and a user input unit configured to input information to the body marker output in a form of a plurality of layers, wherein the user interface unit outputs the body marker in the form of the plurality of layers such that the plurality of layers of the body marker are mapped to the image information in units of the respective regions of the human body, and wherein the controller modifies the information input to the body marker output in the form of the plurality of layers.

2. The ultrasound imaging apparatus of claim 1, wherein the controller divides the obtained image information in units of the regions of the human body using at least one among a line, a plane, and a color.

3. The ultrasound imaging apparatus of claim 1, wherein the controller increases or decreases, according to a user input, sizes of portions of the pieces of image information of the image information in units of the regions of the human body.

4. The ultrasound imaging apparatus of claim 1, wherein the controller divides the obtained image information into at least one among images of a bone, a blood vessel, a nerve, a muscle, and a ligament of the object.

5. The ultrasound imaging apparatus of claim 1, wherein the user interface unit outputs the body marker, which is mapped to the image information in units of the regions of the human body, in the form of at least one among a cross-sectional image, a two-dimensional (2D) image, and a three-dimensional (3D) image.

6. The ultrasound imaging apparatus of claim 1, wherein the information input to the body marker output in the form of the plurality of layers comprises at least one of:
   diagnostic information;
   reference information;
   reference image information; and
   reference annotation information.

7. A method of controlling an ultrasound imaging apparatus, the method comprising:
   obtaining, by the ultrasound imaging apparatus, image information from a transducer converting waves received from an object to electrical signals;
   dividing, by the ultrasound imaging apparatus, the obtained image information into pieces of image information in units of regions of a human body according to an anatomical classification criterion;
   mapping, by the ultrasound imaging apparatus, a body marker to the pieces of image information based on at least one region of a bone, a blood vessel, a nerve, a muscle and a ligament of the human body;
   outputting, to a display unit communicatively connected to the ultrasound imaging apparatus, a result of mapping; and
   inputting information to the body marker output in a form of a plurality of layers,
   wherein the outputting of the result of mapping the body marker to the pieces of image information comprises outputting the body marker in the form of the plurality of layers such that the plurality of layers of the body marker are mapped to the pieces of image information of the image information divided in units of the respective regions of the human body, and
   wherein the mapping of the body marker to the pieces of image information comprises modifying the information input to the body marker output in the form of the plurality of layers.

8. The method of claim 7, wherein the dividing of the obtained image information into the pieces of image information in units of the regions of the human body comprises dividing the obtained image information in units of the regions of the human body using at least one among a line, a plane, and a color.

9. The method of claim 7, wherein the dividing of the obtained image information into the pieces of image information in units of the regions of the human body comprises increasing or decreasing, according to a user input, sizes of portions of the pieces of image information of the obtained image information divided in units of the regions of the human body.

10. The method of claim 7, wherein the dividing of the obtained image information into the pieces of image information in units of the regions of the human body comprises dividing the obtained image information into at least one among images of a bone, a blood vessel, a nerve, a muscle, and a ligament of the object.

11. The method of claim 7, wherein the outputting of the result of mapping comprises outputting the body marker which is mapped to the pieces of image information of the image information divided in units of the regions of the human body, in the form of at least one among a cross-sectional image, a two-dimensional (2D) image, and a three-dimensional (3D) image.

12. The method of claim 7, wherein the inputting of the information to the body marker output in the form of the plurality of layers comprises inputting at least one among diagnostic information, reference information, reference image information, and reference annotation information.

* * * * *